United States Patent [19]

Shimamura et al.

[11] Patent Number: 5,582,826
[45] Date of Patent: Dec. 10, 1996

[54] MONOCLONAL ANTIBODIES WHICH BIND THE GAMMA CHAIN OF HUMAN INTERLEUKIN-2 RECEPTOR

[75] Inventors: Toshiro Shimamura; Junji Hamuro; Harumi Nakazawa; Yuka Kanayama, all of Kawasaki; Kazuo Sugamura, No. 2-8, Asahigaoka 1-chome, Aoba-ku, Sendi-shi, Miyagi-ken; Toshikazu Takeshita, Sendi, all of Japan

[73] Assignees: Ajinomoto Co., Inc., Tokyo; Kazuo Sugamura, Sendai, both of Japan

[21] Appl. No.: 230,843

[22] Filed: Apr. 21, 1994

[30] Foreign Application Priority Data

Apr. 21, 1993 [JP] Japan .................................. 5-094491
Mar. 7, 1994 [JP] Japan .................................. 6-036065

[51] Int. Cl.$^6$ ........................ A61K 39/395; C07K 16/28; C07K 16/24; C12N 5/12
[52] U.S. Cl. ................................ 424/143.1; 530/388.22; 530/388.23; 530/388.1; 530/387.1; 435/240.27
[58] Field of Search ........................... 530/387.3, 388.23, 530/388.22, 387.1, 388.1; 435/240.27; 424/143.1, 144.1, 145.1, 158.1

[56] References Cited

U.S. PATENT DOCUMENTS

| | | | |
|---|---|---|---|
| 4,816,567 | 3/1989 | Cabilly et al. | 530/387.1 |
| 5,084,391 | 1/1992 | Wijdenes et al. | 435/240.27 |
| 5,317,087 | 5/1994 | Cerreiti et al. | 530/350 |
| 5,352,772 | 10/1994 | Smith | 530/350 |

FOREIGN PATENT DOCUMENTS 0578932 4/1993 European Pat. Off. .

OTHER PUBLICATIONS

Waldmann, T. A., Science, 252:1657–1662, 21 Jun. 1991.
Harris, W. J. et al, TIBTECH, 11:42–44, Feb. 1993.
Winter, G. et al., TIPS, 14:139–143, May 1993.
Ishii, N. et al, International Immunology, 6(8):1273–1277, Aug. 1994.
Takeshita, T. et al., Science, 257:379–382, 17 Jul. 1992.

*Primary Examiner*—Lila Feisee
*Assistant Examiner*—Susan A. Loring
*Attorney, Agent, or Firm*—Oblon, Spivak, McClelland, Maier & Neustadt, P.C.

[57] ABSTRACT

A polypeptide which specifically binds to the γ-chain of the human interleukin-2 receptor and selectively inhibits the binding of the γ-chain of human interleukin-2 receptor to the β-chain of the same is provided. The polypeptide has an activity of blocking the human interleukin-2 response. Also provided are an immunosuppressant containing the polypeptide, a DNA gene coding for the polypeptide, a recombinant DNA having the gene, a transformant having the recombinant DNA, and a method for producing the intended polypeptide by incubating the transformant. The novel polypeptide can be used independently, or with substances capable of inhibiting the binding of interleukin-2 to the interleukin-2 receptor, as a medicine for preventing the rejection of grafts after transplantation and also for curing inflammatory diseases such as allergic diseases and autoimmune diseases.

2 Claims, 7 Drawing Sheets

FIG. 2

(a) 5'-CAGGTGAAACTCGAGCAGTCAGG-3'
           CC G    G   T (b) 5'-AAGCTTCATGAGGAGACGGTGACCGTGGTCCC-3'

(c) 5'-ACAGTCATAATGTCCCATATGGACATTCTGCTGACACAGTCTCCA-3'
                    T  C A A     C (d) 5'-GCATCGTCGACTTTGAGCTCCAGCTTGGTCCC-3'

(a) is H-chain 5'-side primer; (b) is H-chain 3'-side primer;
(c) is L-chain 5'-side primer; (d) is L-chain 3'-side primer.
(a) and (c) each have two different bases at five positions.
The underlined part in (b) corresponds to the termination codon.

FIG. 3

```
        <ClaI>              <NdeI><SalI>
5'-CGATTAGTAAGGAGGTTTCATATGTCGACAAATCCTCAGGATCTGGCTCCGAATCCAAAA
3'-  TAATCATTCCTCCAAAGTATACAGCTGTTTAGGAGTCCTAGACCGAGGCTTAGGTTTT

<XhoI><HindIII><BamHI>
   GCACGCAGGTCAAACTCGAGAAGCTTG    -3'
   CGTGCGTCCAGTTTGAGCTCTTCGAACCTAG-5'
```

▲ ; Control antibody added.
■ ; GP-2 added.
□ ; Anti-IL-2R -chain antibody added.
△ ; Anti-IL-2R -chain antibody + GP-2 added.
○ ; Anti-IL-2R -chain antibody added.
● ; Anti-IL-2R -chain antibody + GP-2 added.
◆ ; Anti-IL-2R -chain antibody + anti-IL-2R -chain antibody + GP-2 added.

MONOCLONAL ANTIBODIES WHICH BIND THE GAMMA CHAIN OF HUMAN INTERLEUKIN-2 RECEPTOR

BACKGROUND OF THE INVENTION

1. Field of the Invention

The present invention relates to a polypeptide which specifically binds to the γ-chain of human interleukin-2 receptor to selectively inhibit the binding of the γ-chain of human interleukin-2 receptor to the β-chain of the same. The polypeptide has the biological activity of blocking the human interleukin-2 response. The invention also relates to an immunosuppressant containing the polypeptide, a DNA coding for the polypeptide, a recombinant DNA having the gene, a transformant having the recombinant DNA, and a method for producing the intended polypeptide by cultivating the transformant.

The polypeptide of the present invention is a valuable substance which is usable, independently or along with substances capable of inhibiting the binding of interleukin-2 to interleukin-2 receptor, as a medicine effective in preventing the rejection after transplantation and also in curing inflammatory diseases such as allergic diseases and autoimmune diseases, the possibility that interleukin-2 will participate in the rejection and also in such inflammatory diseases having been suggested. "Interleukin-2" may be hereinafter referred to as "IL-2".

2. Discussion of the Background

Now that surgical techniques for transplantation have been improved noticeably, success in transplantation essentially depends upon inhibiting the rejection of a graft after the operation. The rejection phenomenon results from a series of immunoreactions occurring through the interaction of the graft with organs of the recipient which have recognized the graft as foreign matter and reject them. Therefore, so-called immunosuppressants such as various steroids, azathiopurine, methotrexate and 6-mercaptopurine have heretofore been used as rejection-inhibiting medicines. However, since the safety range of such medicines is narrow and their effects are weak, extreme improvement in the take of grafts in recipients could not be attained.

Using cyclosporin A, a drug which has been developed recently, the take of grafts in recipients has improved surprisingly. However, it has been recognized that cyclosporin A has serious nephrotoxicity, which has obliged us to limit its use. Given this situation, it is desirable to develop more safe, more specific and more effective immunosuppressants.

IL-2 is a protein that is produced by helper T-cells and is an extremely important factor for the host defense machinery, having various functions of broad range. For example, it is involved in induction of proliferation and differention of killer T-cells and induction of differention of B cells in living bodies. It has been said that killer T-cells activated by IL-2, etc. participate strongly in the host vs. graft reaction (HVG reaction) or the graft vs. host reaction (GVH reaction) which is considered to be the key to the take of grafts in transplantation of organs or bone marrow.

On the other hand, it is considered that autoimmune diseases are caused by an imbalance of the immune system in the living body, resulting in the body attacking itself. In particular, there is a great possibility that excess production of factors participating in the immune system, such as IL-2, as well as excess reaction thereto, will essentially cause an imbalance of the immune system.

Thus, it is possible that if the IL-2 response may be selectively and effectively inhibited, then rejection after transplantation may be prevented and autoimmune diseases may be cured. In fact, there have been published reports in which IL-2 and a cytotoxin were fused together to prepare a polypeptide capable of selectively damaging IL-2 responding cells having IL-2 receptors. The polypeptide was administered to a rat with adjuvant arthritis, which is one of the animal models with an autoimmune disease, with the result that the onset of the symptoms of arthritis was delayed in the rat and the presented symptoms of arthritis were slight. The report further revealed that when the polypeptide was administered, during the transplantation, to a mouse that had received a cardiac graft by transplantation from an allogenic mouse, then rejection of the transplanted cardiac graft in the recipient mouse was inhibited. (Proc. Natl. Acad. Sci. USA, Vol. 86, page 1008, 1989.)

However, the polypeptide obtained by fusing IL-2 and a cytotoxin has a short half-life period in blood so that a large amount of the polypeptide must be dosed in order to attain the intended effect, which, however, also causes some harmful side effects. Therefore, the development of a medicine which is safer, more specific and more effective in inhibiting the IL-2 response has been desired.

Heretofore, it has been known that the IL-2 receptor on IL-2 responding cells is composed of two glycoprotein molecules, one being an α-chain having a molecular weight of about 55 kd and the other being a β-chain having a molecular weight of about 75 kd. The dissociation constant of binding between these molecules and IL-2 is $10^{-8}$M for the α-chain and $10^{-9}$M for the β-chain, respectively. It has been considered that, when both the α-chain and the β-chain are bound to IL-2 at the same time, then the resulting association has high-affinity binding with a dissociation constant of $10^{-12}$M.

However, it has recently been clarified that, even when a human β-chain cDNA is transfected into mouse non-lymphocytic cells, it does not bind to IL-2, and that even when both human α-chain and β-chain cDNA's are transfected into the same, they may bind to IL-2 only to an intermediate degree without forming any high-affinity binding to the same. (Science, Vol. 244, page 551, 1989.) Hence, the existence of a third molecule different than the α-chain and the β-chain, which is crucial for the binding to IL-2, has been suggested.

We, the present inventors have cloned a gene coding for a glycoprotein molecule having a molecular weight of 64 kd which is the third molecule constituting the IL-2 receptor complex (hereinafter referred to as IL-2 receptor γ-chain) (Japanese Patent Application No. 4-104947 and Science, Vol. 257, page 379, 1992) by which the IL-2/IL-2 receptor system has been clarified completely.

Specifically, it has been shown that the association formed by transfection of both human β-chain and γ-chain cDNA's into mouse non-lymphocytic cells shows an intermediate degree of binding between them, which was previously attributed to the β-chain only; and that the transfection of all human α-chain, β-chain and γ-chain cDNA's into the same cell gives high-affinity binding between them. The latter effect has previously been attributed to the α-chain and the β-chain only. In addition, it has been shown that the internalization of an IL-2/IL-2 receptor complex into cells, which is considered to be a prerequisite for signal transduction for IL-2, does not occur in cells expressing only the β-chain or in cells expressing both the α-chain and the β-chain, but may occur in cells additionally expressing the γ-chain. Accordingly, the present inventors have clarified for the first time that the IL-2 receptor γ-chain molecule is not a molecule which merely defines its binding to IL-2, but is a molecule which is indispensable for the signal transduction triggered by IL-2.

It is known that the IL-2 receptor γ-chain molecule binds to the extracellular site in the IL-2 receptor β-chain in the presence of IL-2. (Science, Vol. 257, page 379, 1992.) Therefore, it is considered that if the binding between the β-chain and the γ-chain were inhibited, the β-chain alone could not bind to IL-2, or both the α-chain and the β-chain might bind to IL-2 to some intermediate degree while the IL-2-signal transduction would be blocked. Namely, if the binding between the IL-2 receptor β-chain and the IL-2 receptor γ-chain on IL-2 responding cells is inhibited, the IL-2 signal transduction can be completely blocked and the cells then become unresponsive to IL-2. Therefore, by the inhibition, the rejection of transplanted tissue, in which IL-2 is believed to participate, can be prevented and autoimmune diseases, in which IL-2 is considered to also actively participate, can be cured. Up to the present time however, no substance having the activity of inhibiting the binding between the IL-2 receptor β-chain and the IL-2 receptor γ-chain was known.

SUMMARY OF THE INVENTION

Accordingly, an object of the present invention is to provide a polypeptide which specifically binds to the γ-chain of the human IL-2 receptor, to selectively inhibit the binding of the γ-chain of the human IL-2 receptor to the β-chain of the same, therefore having an activity of blocking the human IL-2 response, and also an immunosuppressant containing the polypeptide, a DNA coding for the polypeptide, a recombinant DNA having the DNA, a transformant having the recombinant DNA, and a method for producing the intended polypeptide by cultivating the transformant.

The polypeptide of the present invention is a valuable substance which is usable, independently or along with substances capable of inhibiting the binding of IL-2 to the IL-2 receptor, as a medicine effective in preventing the rejection of grafts after transplantation and also in curing inflammatory diseases such as allergic diseases and autoimmune diseases, due to the likelihood that IL-2 participates in the rejection process and also in such inflammatory diseases.

We, the present inventors have repeated assiduous studies so as to attain the above-mentioned object and, as a result, have found that the intended polypeptide, which specifically binds to the γ-chain of the human IL-2 receptor, selectively inhibits the binding of the γ-chain of the human IL-2 receptor to the β-chain of the same, therefore having an activity of blocking the human IL-2 response. On the basis of this finding, we have completed the present invention.

Accordingly, the present invention provides a polypeptide which specifically binds to the γ-chain of human IL-2 receptor to selectively inhibit the binding of the γ-chain of human IL-2 receptor to the β-chain of the same, therefore having an activity of blocking the human IL-2 response, and also an immunosuppressant containing the polypeptide, a DNA coding for the polypeptide, a recombinant DNA having the DNA, a transformant having the recombinant DNA, and a method for producing the intended polypeptide by cultivating the transformant.

First, there is provided in accordance with the present invention a polypeptide which specifically binds to the γ-chain of the human interleukin-2 receptor, therefore having an activity of blocking the human IL-2 response.

As one preferred embodiment, the polypeptide is a mouse monoclonal antibody.

As another preferred embodiment, the monoclonal antibody is produced by cells of GP-2 or GP-4.

As still another preferred embodiment, the monoclonal antibody is produced by cells of TUGh4, TUGh5 or AG14.

As still another preferred embodiment, the polypeptide contains only the variable region of the monoclonal antibody.

As still another preferred embodiment, the polypeptide has an amino acid sequence of Sequence No. 2 mentioned hereinafter.

As still another preferred embodiment, the polypeptide has an amino acid sequence of Sequence No. 4 mentioned hereinafter.

As still another preferred embodiment, the polypeptide has an amino acid sequence of Sequence No. 2 mentioned hereinafter, from which its N-terminal Met has been deleted.

As still another preferred embodiment, the polypeptide has an amino acid sequence of Sequence No. 4 mentioned hereinafter, from which its N-terminal Met has been deleted.

As still another preferred embodiment, the polypeptide has an amino acid sequence of Sequence No. 2, (1) of which a part has been deleted, (2) of which a part has been substituted by a different amino acid sequence, (3) to which amino acid residue(s) or peptide(s) has/have been added, or (4) of which a part has been acetylated, amidated or modified with polyethylene glycol(s).

As still another preferred embodiment, the polypeptide has an amino acid sequence of Sequence No. 4, (1) of which a part has been deleted, (2) of which a part has been substituted by a different amino acid sequence, (3) to which amino acid residue(s) or peptide(s) has/have been added, or (4) of which a part has been acetylated, amidated or modified with polyethylene glycol(s).

As still another preferred embodiment, the polypeptide is such that the constant region of the mouse monoclonal antibody has been changed into the constant region of a human antibody.

As still another preferred embodiment, the polypeptide is such that the constant region and the framework sequence of the variable region of the mouse monoclonal antibody have been changed into the constant region and the framework sequence of a human antibody, respectively.

Secondly, also provided is an immunosuppressant containing the novel polypeptide.

As one preferred embodiment, the immunosuppressant contains the novel polypeptide along with an anti-human interleukin-2 receptor α-chain antibody and/or an anti-human interleukin-2 receptor β-chain antibody.

As another preferred embodiment, the immunosuppressant contains the novel polypeptide along with (a) a polypeptide containing the variable region of an anti-human interleukin-2 receptor α-chain antibody, a polypeptide derived from the polypeptide by deleting a part of it, a polypeptide derived from the polypeptide by substituting a part of it by other amino acid(s), or a polypeptide derived from the polypeptide by adding other amino acid residue(s), other polypeptide(s) or other substance(s) thereto, and/or (b) a polypeptide containing the variable region of an anti-human interleukin-2 receptor β-chain antibody, a polypeptide derived from the polypeptide by deleting a part of it, a polypeptide derived from the polypeptide by substituting a part of it by other amino acid(s), or a polypeptide derived from the polypeptide by adding other amino acid residue(s), other polypeptide(s) or other substance(s) thereto.

As still another preferred embodiment, the immunosuppressant contains the novel polypeptide along with an anti-human interleukin-2 receptor α-chain antibody containing the human constant region and/or an anti-human interleukin-2 receptor β-chain antibody containing the human constant region.

As still another preferred embodiment, the immunosuppressant contains the novel polypeptide along with an anti-human interleukin-2 receptor α-chain antibody containing the human constant region and the framework sequence of the human variable region and/or an anti-human interleukin-2 receptor β-chain antibody containing the human constant region and the framework sequence of the human variable region.

Thirdly, also provided is a DNA coding for the novel polypeptide.

As one preferred embodiment, the DNA has a nucleotide sequence of Sequence No. 1.

As another preferred embodiment, the DNA has a nucleotide sequence of Sequence No. 3.

Fourthly, also provided is a recombinant DNA having the novel DNA.

Fifthly, also provided is a transformant having the novel recombinant DNA.

As one preferred embodiment, the transformant is of Escherichia coli or eukaryotic cells.

Sixthly, also provided is a method of producing the novel polypeptide by cultivating the novel transformant to produce the polypeptide followed by collecting the polypeptide.

BRIEF DESCRIPTION OF THE DRAWINGS

FIG. 2 shows the sequences of primers used in Example 3.

FIG. 3 shows the DNA sequence of the linker used in Example 4 for linking the V-region of the L-chain and the V-region of the H-chain.

DETAILED DESCRIPTION OF THE PREFERRED EMBODIMENTS

Figure 1:
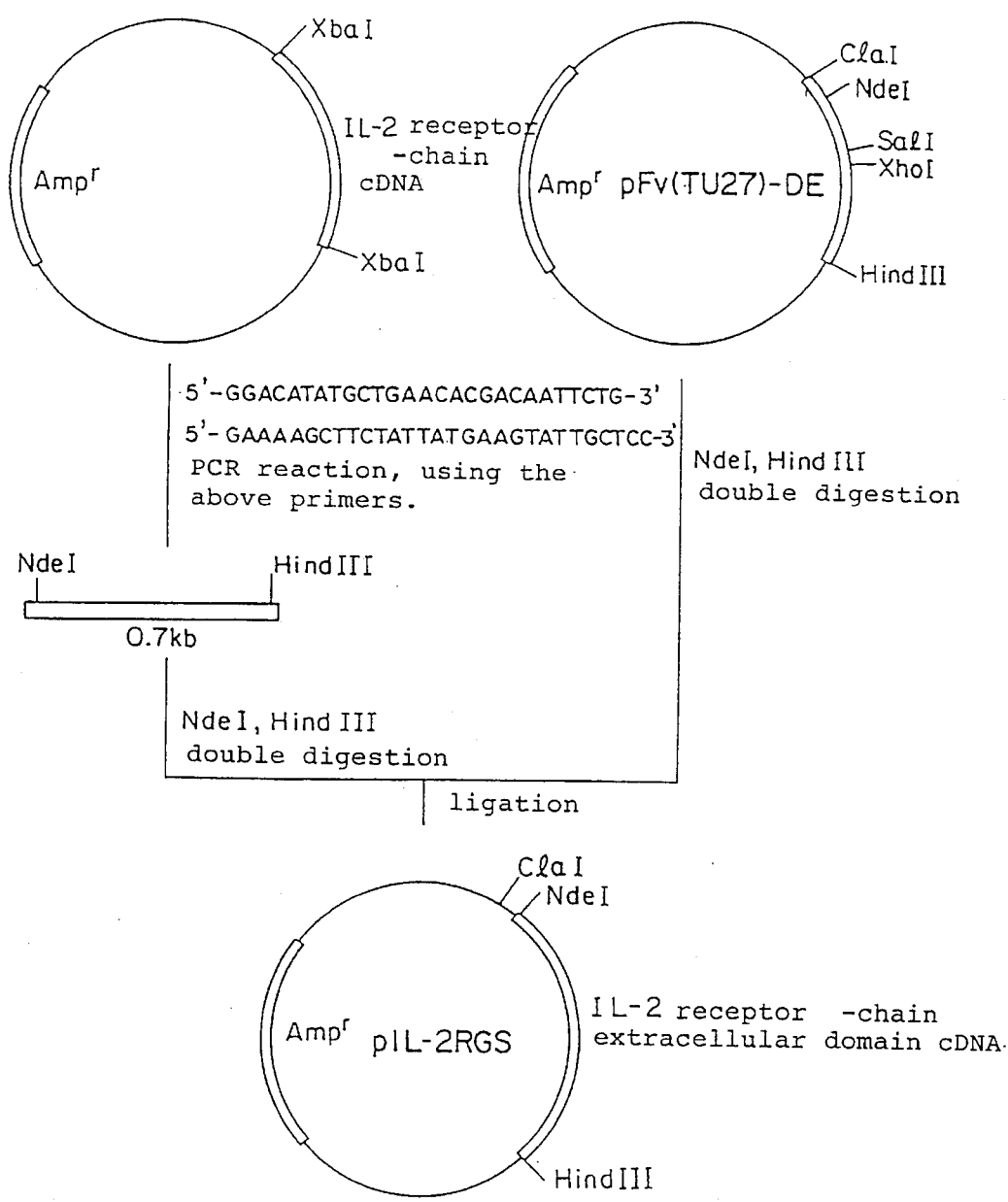
FIG. 1 shows a process of constructing plasmid pIL-2 RGS.

In accordance with the present invention, there is provided a polypeptide which specifically binds to the γ-chain of the human IL-2 receptor to selectively inhibit the binding of the γ-chain of the human IL-2 receptor to the β-chain of the same, therefore having an activity of blocking the human IL-2 response.

We, the present inventors first produced a number of hybridomas capable of producing a mouse monoclonal antibody that specifically binds to the γ-chain of human IL-2 receptor, from which we have selected the hybridoma clone that produces a mouse monoclonal antibody having the activity of inhibiting the human IL-2 response. A method of preparing the hybridoma clone that produces a mouse anti-human IL-2 receptor γ-chain monoclonal antibody will be described below.

The hybridomas are produced by fusing myeloma cells and antibody-producing cells. Useful antibody-producing cells include cells of the spleen or the lymph node of an animal, such as mouse or rat, that has been immunized with a recombinant human IL-2 receptor γ-chain molecule. Useful immunizing substances include single, recombinant human IL-2 receptor molecules, fused molecules composed of the molecule and other protein(s), and polypeptides fragments of the IL-2 receptor. Above all, recombinant human IL-2 receptor molecules having only the extracellular region are especially efficiently used. In place of recombinant human IL-2 receptor γ-chain molecules, also usable are human cells expressing the human IL-2 receptor γ-chain molecule as well as mouse cells, etc. into which a gene coding for a human IL-2 receptor γ-chain molecule has been transfected to be able to produce the γ-chain molecule therein by biosynthesis. In addition, also usable are the γ-chain itself that has been purified from such cells, as the immunogen.

The species of the animals from which the antibody-producing cells and the myeloma cells are derived may be different from each other, provided that both cells may be fused together, but in general it is preferable if both cells are derived from the same species. One preferred mode for carrying out the present invention involves hybridomas obtained by fusing cells of the spleen or lymph node of a mouse that has been immunized with a polypeptide having only the extracellular region of a human recombinant IL-2 receptor γ-chain molecule and mouse myeloma cells.

For example, hybridomas can be obtained by fusing cells of the spleen of a Balb/c mouse that has been immunized with a polypeptide having only the extracellular region of a human recombinant IL-2 receptor γ-chain molecule, as suspended in a physiological saline solution, and myeloma cells SP2/0-Ag14 of a Balb/c mouse. Using these hybridomas, an excellent result has been obtained, as shown in the example below.

A polypeptide having only the extracellular region of human recombinant IL-2 receptor γ-chain molecule may be obtained by cultivating a transformant having an expression plasmid vector containing a gene coding for the molecule.

As the transformant, any of the procaryotic cells, such as E. coli, are usable as well as eukaryotic cells such as CHO cells.

As the myeloma cells, in addition to SP2/0-Ag14, other usable cells include those from 8-azaguanine-resistant cell strains, such as mouse myeloma cells X63-Ag8-6.5.3, P3-X63-Ag8-U1, P3-X63-Ag8, P3-NSI/1-Ag4-1 and MPC11-4.5.6.TG.1.7, rat myeloma cells 210.RCY.Ag1.2.3, human myeloma cells SKO-007 and GH15006TG-A12. The formation of the hybridomas as well as the selection from among them of the hybridoma clones which produce a monoclonal antibody capable of binding to the γ-chain molecule of IL-2 receptor and therefore having an activity of blocking the IL-2 response may be conducted, for example, as mentioned below. First, the antibody-producing cells and the myeloma cells are fused together using polyethylene glycol or Sendai viruses, etc. Only the fused hybridomas may grow in a medium containing hypoxanthine, thymidine and aminopterin (HAT medium). Not all of the hybridomas obtained produce antibodies and not all of the antibody-producing hybridomas produce the intended antibody. Therefore, a hybridoma clone that produces a monoclonal antibody capable of binding to the γ-chain molecule of IL-2 receptor and having an activity of blocking the IL-2 response must be selected from among them.

The selection may be conducted, for example, according to the process mentioned below. The binding of the antibody that has been produced in the supernatant of the hybridoma culture of mouse L929 cells into which a gene coding for a human IL-2 receptor γ-chain molecule has been transfected and which therefore express the peptide (hereinafter referred to as Lγ cells) and the binding of the same to mouse L929 cells into which a gene coding for a human IL-2 receptor β-chain molecule has been transfected and which therefore express the peptide (hereinafter referred to as Lβ cells) are measured. Those in which the binding of the antibody to the former is high while that to the latter is low are selected. The hybridomas thus selected produce an antibody capable of specifically binding to the γ-chain molecule of the IL-2 receptor.

For measurement of the binding of the antibody to the cells, any suitable radioimmunoassay using a radioisotope-labeled anti-mouse immunoglobulin antibody may be used, as well as fluorescent immunoassays using a fluorescent dye-labeled anti-mouse immunoglobulin antibody, etc. As to the cells to be used for the screening, any combination comprised of cells that express the human γ-chain and cells that do not express the same may be employed.

Since not all the antibodies capable of specifically binding to the γ-chain molecule of IL-2 receptor have an activity of blocking the IL-2 response, hybridomas that produce an antibody having an activity of blocking the IL-2 response are selected from among those that produce the antibody to the γ-chain molecule of IL-2 receptor, in accordance with the process mentioned below.

Precisely, the supernatant of the hybridoma culture is added to ILT-Mat cells of a human adult T-cell leukemia virus-infected T-cell line having a human IL-2 -dependent growth activity, whereupon the growth-inhibiting activity of the hybridomas, if any, against the ILT-Mat cells is measured. (Journal of Experimental Medicine, Vol. 169, page 1323. 1989) If the hybridomas have the growth-inhibiting activity, they are the intended monoclonal antibody-producing cells. Other means of selecting the hybridomas that produce the antibody having the activity of blocking the IL-2 response from among the hybridomas that produce the antibody to the γ-chain molecule of IL-2 receptor may also be employed, provided that they are processes of measuring the biological activity of human IL-2 using human cells, apart from the process of using ILT-Mat cells. Examples of hybridoma clones thus obtained include cells of GP-2 (FERM BP-4641), GP-4 (FERM BP-4640), TUGh4 (FERM BP-4642), TUGh5 (FERM BP-4643) and AG14(FERM BP-4648) as deposited on Apr. 15, 1994 with the National Institute of Bioscience and Human Technology, Agency of Industrial Science and Technology, 1-3 Higashi 1 chome, Tsukuba-shi, Ibaraki-ken, JAPAN 305.

For producing a large amount of the monoclonal antibody, it is possible that GP-2 cells (FERM BP-4641), GP-4 (FERM BP-4640), TUGh4 cells (FERM BP-4642), TUGh5 (FERM BP-4643) or AG14 cells (FERM BP-4648) are injected intraperitoneally into a tissue-adaptable animal, a thymoprival nude mouse or the like and grown therein and the antibody produced in the ascites of the animal is recovered and purified by salting-out, ion-exchanging chromatography, etc.

Next, a polypeptide comprising the V region of the monoclonal antibody capable of binding to the γ-chain of IL-2 receptor and therefore having an activity of blocking the IL-2 response may be produced, for example, in accordance with the process mentioned below.

First, a total RNA is extracted from the hybridoma clone that produces the monoclonal antibody capable of binding to the γ-chain of IL-2 receptor and therefore having an activity of blocking the IL-2 response to obtain the gene (cDNA) coding for the V-region of the monoclonal antibody. We, the present inventors have assiduously designed the process for obtaining the intended cDNA as rapidly as possible and have obtained the cDNA coding for the V region of the antibody in accordance with the process mentioned below.

First, on the basis of the nucleotide sequences of the H-chain and the L-chain of a mouse IgG, of which the nucleotide sequence of the gene has already been reported, four kinds of DNA molecules (primer DNA's) each having a nucleotide sequence comprised of from 20 to 30 bases, which are highly common to the 5'-terminal and the 3'-terminal of the genes of the respective V-regions of the chains, are designed. The 5'-side and the 3'-side hereinafter referred to are based on the sense strands of the H-chain V-region gene and the L-chain V-region gene. The 5'-side primer is a DNA molecule having the sequence on the sense strand, while the 3'-side primer is a DNA molecule having the complementary sequence at the 3'-side of the sense strand.

Next, an ATG sequence which is a translation-initiating codon is added to the 5'-side of the thus-designed L-chain V-region 5'-side primer, while a translation-terminating codon is added to the 3'-side of the 3'-side primer of the H-chain.

As a matter of course, the ATG sequence may be added to the 5'-side of the H-chain V-region 5'-side primer while the terminating codon added to the 3'-side of the L-chain V-region 3'-side primer is any of TAA, TAG and TGA. In the example of the present invention which will be mentioned hereinafter, TGA was used as the terminating codon.

A suitable restriction enzyme site into which an expression vector will be inserted is previously introduced into the 5'-terminals of the respective primer DNA's of the H-chain and the L-chain (the 5'-terminal as referred to herein indicates the 5'-terminal based on the primer molecule for the 3'-side primer). The thus-designed primer DNA is chemically synthesized, using a DNA synthesizer or the like.

Next, a total RNA is extracted from the obtained hybridoma by a known method, a single-stranded cDNA is formed from a reverse transcripitase and the 3'-side primer DNA, and only the DNA fragments each coding for the V-region of the H-chain of the antibody and the V-region of the L-chain of the same are selectively amplified and collected by a polymerase chain reaction method (PCR method—see Science, Vol. 230, page 1350, 1985) using a Taq polymerase and using the 5'-side primer DNA and the 3'-side primer DNA.

In order that the gene coding for the H-chain V-region and the gene coding for the L-chain V-region be expressed in *E. coli*, etc. and produce a polypeptide comprising only the functional antibody V-region, the two genes are separately inserted into two different vectors so as to attain the intended expression therein. Alternatively, both genes are inserted into one vector, also so as to attain the intended expression therein, and thereafter the polypeptide comprising the H-chain V-region and the polypeptide comprising the L-chain V region may be assembled together. However, it is known that the efficiency of the process is extremely poor. (See Science, Vol. 240, page 1038, 1988.)

Natural antibodies are composed of a combination of two molecules to be obtained by binding the H-chain and the L-chain together via SS-crosslinking by a covalent bond. Namely, it has a structure of a dimer, in which the H-chains of the respective molecules together form a SS bond. The position of the SS-crosslinking between the H-chain and the L-chain is on the constant region (hereinafter referred to as the C-region), while the H-chain V-region and the L-chain V-region are bound to each other by non-covalent bonding interactions. Therefore, when a polypeptide comprising the H-chain V-region and a polypeptide comprising the L-chain V-region are assembled into a polypeptide comprising only the antibody V-region, the association of the two molecules must rely only upon non-covalent bonding. This is probably why the efficiency in forming the functional molecule is poor. Recently, however, there has been developed a novel technique for linking a polypeptide comprising the H-chain V-region and a polypeptide comprising the L-chain V-region with a linker to give a single-stranded functional molecule. (Science, Vol. 242, page 423, 1988.)

We, the present inventors, having applied the technique, have succeeded in the expression of a polypeptide comprising only the V-region of a functional, single-stranded anti-IL-2 receptor γ-chain antibody. First, an expression vector is constructed, comprising a DNA containing a promoter region, a DNA containing a ribosome-binding region, a DNA containing a restriction enzyme site that has been introduced into the ATG sequence-added 5'-side primer, a DNA containing a restriction enzyme site that has been introduced into the 3'-side primer of the same chain, a DNA coding for a linker peptide having a suitable length that is to link the antibody L-chain V-region and the antibody H-chain V-region, a DNA containing a restriction enzyme site that has been introduced into the 5'-side primer having no ATG sequence, a DNA containing a restriction enzyme site that has been introduced into the 3'-side primer of the same chain, and last a DNA containing a terminator region, that have been arranged in this order from the upper stream.

Where the DNA coding for the H-chain V-region that has been amplified by PCR and the DNA coding for the L-chain V-region are both inserted, attention should be paid in order to ensure that the translations of the DNA coding for the linker peptide and the DNA coding for the V-region are not mismatched.

The origin of the promoter to be employed in the present invention can vary. Useable promoters include the trp promoter, tac promoter, trc promoter and lac promoter from *E. coli*; λP$_L$ promoter and λP$_R$ promoter from λ phage; and also SV40 promoter, Moloney LTR promoter and CMV promoter from eukaryotic cells. Examples of usable ribosome-binding regions are trpL, trpE and lacZ from *E. coli*, and the ribosome-binding region of CII protein from λ phage. In addition, chemically synthesized DNA sequences may also be employed, as the case may be. If desired, the expression vector may have two or more ribosome-binding regions so that a large amount of granules of the intended polypeptide accumulate in the cells of *E. coli*.

The linker peptide for linking the polypeptide comprising the H-chain V-region and the polypeptide comprising the L-chain V-region may have any sequence, provided that the polypeptide comprising the complete antibody V-region obtained by linking the two polypeptides with it is functional. However, in order to minimize any harmful side effects of the functional polypeptide when administering it to living bodies, it is desirable that the sequence of the linker peptide be as short as possible and have no peculiar structure.

Examples of useful terminators include the trpA terminator, rrnB terminator and recA terminator from *E. coli*. It is generally desired that the number of copies of the expression plasmid be as large as possible, and the pUC replication starting point is preferred to the pBR replication starting point.

The DNA coding for the polypeptide comprising the H-chain V region that has been amplified by PCR and the DNA coding for the polypeptide comprising the L-chain V-region are inserted into the thus-constructed expression vector to obtain a recombinant DNA. After the insertion, the recombinant DNA is used to transform a host by conventional methods, whereby the gene on the recombinant DNA may be expressed in the host. As the host, any of procaryotes and eukaryotes are employable. Examples of procaryotes include *E. coli*, *Bacillus subtilis*, etc. As examples of eukaryotes, mentioned are yeast, CHO cells, etc. The preferred hosts are procaryotes and most preferred is *E. coli*.

For transformation of the host with the recombinant DNA, any known method may be employed. In the case of *E. coli*, cells in the logarithmic growth stage are treated with 50 mM of calcium chloride in ice for about 30 minutes to modify the structure of the cell wall and subsequently the plasmid DNA is injected thereinto. After about 10 minutes, the cells are heat-treated at 30° C. to 42° C. for 2 minutes. Then, a medium is added thereto and the cells are incubated therein at 30° C. to 37° C. for about 60 minutes, whereby the recombinant DNA is introduced into the cells.

By incubating the cells that have been transformed with the recombinant DNA in the medium, the intended polypeptide comprising only the V-region of the monoclonal antibody to the β-chain of IL-2 receptor may be accumulated in the cells or in the medium. The medium may be any known one in which the cells may grow, and the conditions for the incubation may also be known ones. After the incubation, the intended polypeptide comprising only the V-region of the monoclonal antibody may be collected by a known method.

A polypeptide in which the C-region of the mouse monoclonal antibody capable of binding to the γ-chain of IL-2 receptor and therefore having an activity of blocking the IL-2 response has been changed into the C-region of a human antibody, and a polypeptide in which the constant region and the framework sequence of the V-region (hereinafter referred to as FR) of the mouse monoclonal antibody have been changed into the C-region and the FR, respectively, of a human antibody may be produced by the methods mentioned below.

First, a DNA having a length of from 20 to 30 bases corresponding to the nucleotide sequence of the 5'-terminal of the gene coding for the signal peptide of the H-chain or L-chain of the antibody is synthesized. A restriction enzyme site in which the DNA is inserted downstream of the promoter region of the expression vector is previously introduced into the 5'-terminal of the DNA to be synthesized. Subsequently, a DNA having a length of from 20 to 30 bases corresponding to the complementary sequence of the nucleotide sequence of the 3'-terminal of the gene coding for the V-region of the H-chain or L-chain of the antibody is synthesized. Also prior to the synthesis, a restriction enzyme site, at which the C-region cDNA of a human antibody is bound to the DNA, is previously arranged at the 3'-terminal of the DNA.

From the hybridoma that produces the mouse monoclonal antibody having an activity of blocking the IL-2 response, a total RNA is prepared by conventional methods, from which is produced a single-stranded cDNA using a reverse transcriptase or the like. Afterwards, by PCR reaction using the thus-synthesized DNA as the primer, a DNA fragment coding for the signal peptide for the H-chain or L-chain and the V-region of the antibody is obtained.

In the same manner as above, the C-region gene of a human antibody may be obtained by preparing a total RNA from a human B-cell line or a human plasma cell line that produces an antibody and then forming a cDNA from the RNA using a reverse transcriptase or the like followed by subjecting the cDNA to PCR using a previously prepared DNA corresponding to the nucleotide sequence of the part of the 5'-terminal or the 3'-terminal of the C-region of the H-chain or the L-chain of the antibody. In the process, the same restriction enzyme site as the site that has been introduced into the 3'-side primer employed for obtaining the DNA fragment coding for the signal peptide of the H-chain or the L-chain and the V-region of the antibody is arranged at the outside of the 5'-terminal of the 5'-side primer; while a restriction enzyme site, at which the gene is inserted into the downstream of the promoter region of the expression vector, is arranged at the outside of the 5'-terminal of the 3'-side primer. Accordingly, the structure of the gene is so designed that the frames are not mismatched at the joint of the 3'-terminal of the V-region and the 5'-terminal of the C-region. The class or subclass of the antibody to be prepared may be selected freely in accordance with the use and the object, by preparing a total RNA from the cells producing the antibody of the intended class or subclass followed by preparing the corresponding DNA coding for the C-region.

The thus-obtained DNA fragment coding for the signal peptide and the V-region of the mouse antibody and the DNA fragment coding for the C-region of the human antibody each are cut with the restriction enzyme corresponding to the restriction enzyme site that has been introduced into the respective fragments, and they are then mixed. Next, these DNA's are inserted into an expression vector expressible in animal cells, the expression vector having been cut with a restriction enzyme. The restriction enzyme to be used for cutting the expression vector is one which may yield the cut ends corresponding to those of the restriction enzyme site that is introduced into the DNA fragment coding for the signal peptide and the V-region of the mouse antibody and into the DNA fragment coding for the C-region of the human antibody from the PCR primer. Where the DNA fragment coding for the signal peptide and the V-region of the mouse antibody codes for those of the H-chain, it must be inserted into the expression vector along with the DNA fragment coding for the C-region of the human antibody H-chain. Similarly, where the DNA fragment coding for the signal peptide and the V-region of the mouse antibody codes for those of the L-chain, it must be inserted into the expression vector along with the DNA fragment coding for the C-region of the human antibody L-chain.

Finally, the expression vectors into which the DNA fragment coding for the signal peptide and the V-region of the mouse antibody and the DNA fragment coding for the C-region of the human antibody have been inserted each in the right direction are selected.

Both of the thus-prepared expression vectors each containing a gene coding for the signal peptide and the V-region of the mouse antibody of the H-chain or L-chain and a gene coding for the C-region of the human antibody are transfected into animal cells by known methods. As the host where the expression vectors are expressed, any host other than animal cells may also be employed. In this case, however, the vectors to be transfected into them shall be those which may be expressed in them.

After the transfection, the cells are cloned, and the binding activity of the antibody, which has been produced in the supernatant of the culture, to the γ-chain of IL-2 receptor is measured. Accordingly, the intended polypeptide where the C-region of the mouse monoclonal antibody capable of binding to the γ-chain of IL-2 receptor and therefore having an activity of blocking the IL-2 response has been changed to the C-region of the human antibody is obtained.

A polypeptide where the C-region and the FR of the V-region of the mouse monoclonal antibody has been changed into the C-region and the FR, respectively, of a human antibody may be produced by the process mentioned below. (Medical Immunology, Vol. 22, No. 6, page 628. 1991) First, the amino acid sequence derived from the prepared DNA coding for the V-region of the mouse monoclonal antibody and the amino acid sequence of the V-region of a known human antibody are subjected to homology reference, by which the sequences with the highest homology are selected both for the H-chain and the L-chain. Next, the signal peptide and the FR part of the V-region are so designed that they may have the selected amino acid sequences of the human antibody, while the other V-region is so designed that it may have the amino acid sequence of the mouse monoclonal antibody. Then, DNA fragments coding for the peptide are designed and synthesized both for the H-chain and the L-chain. In this process, the DNA fragments are divided into segments each having a length of approximately from 30 to 40 bases while approximately from 5 to 7 bases are made to overlap at the joints of the segments, and these are synthesized to have a complementary sequence to the original sequence on alternate segments. At the outside of the 5'-terminal of the signal peptide and the 3'-terminal of the V-region are arranged an expression vector and a restriction enzyme site at which the DNA fragment is bound to the human C-region. These synthetic DNA fragments are mixed and subjected to PCR, and the recovered DNA fragments coding for the signal peptide and the V-region of the H-chain and the L-chain of the antibody are cut with the restriction enzyme corresponding to the introduced restriction enzyme site. Using the similar restriction enzyme, the DNA fragments coding for the signal peptide and the V-region of the H-chain and the L-chain are cut and separated from the previously prepared vectors that express the polypeptides where the C-region of the H-chain and the L-chain of the mouse monoclonal antibody have been changed into the C-region of the human antibody, and they are substituted for the previously prepared DNA fragment coding for the signal peptide and the V-region. The thus-constructed recombinant DNA is transfected into animal cells by the same process as that mentioned above, and the cells that express the intended polypeptide are selected also by the same process as above. Accordingly, the intended polypeptide where the C-region and the FR of the V-region of the mouse monoclonal antibody capable of binding to the γ-chain of IL-2 receptor and therefore having an activity of blocking the IL-2 response have been changed into the V-region and the FR, respectively, of the human antibody is obtained.

The polypeptide of the present invention specifically binds to the γ-chain of IL-2 receptor and therefore has an activity of blocking the response of IL-2, and is effective in preventing the rejection of organs after transplantation and in curing autoimmune diseases.

The monoclonal antibody of the present invention is not defined only as the monoclonal antibody produced by the hybridoma clones obtained herein, but includes any other monoclonal antibody capable of binding to the γ-chain of IL-2 receptor and therefore having an activity of blocking the IL-2 response. In addition, a chimera antibody prepared by changing the C-region of the monoclonal antibody of the present invention into a human C-region by known methods and an antibody prepared by changing the FR of the V-region of the same into a human FR, are also within the scope of the monoclonal antibody of the present invention, provided that they bind to the γ-chain of IL-2 receptor and therefore have an activity of blocking the IL-2 response.

The structure of the polypeptide of the present invention has, for example, the sequence of Sequence No. 2 or No. 4 shown in Table of Sequences, which, however, are not intended to be limiting. The present invention includes any other polypeptide capable of binding to the γ-chain of IL-2 receptor and therefore having an activity of blocking the IL-2 response. For instance, it includes (1) a polypeptide having the structure of Sequence No. 2 or No. 4 in which one or more amino acid residues have been substituted by other amino acid residue(s), (2) a polypeptide having a continuous amino acid sequence of Sequence No. 2 or No. 4 in which one or more amino acid residues have been deleted from the N-terminal and/or the C-terminal, (3) a polypeptide having a structure of Sequence No. 2 or No. 4 in which one or more amino acid residues have been added to the N-terminal and/or the C-terminal, (4) a polypeptide having a structure of Sequence No. 2 or No. 4 in which one or more amino acid residues have been acetylated, amidated or modified with polyethylene glycol(s), provided that they bind to the γ-chain of IL-2 receptor and therefore have an activity of blocking the IL-2 response.

In particular, Met at the N-terminal of the polypeptide having a structure of Sequence No. 2 or No. 4 in the Sequence Listing is often cut during the process of expressing it using microorganisms or during the process of purifying it, with the result that its N-terminal is changed into Asp. The resulting polypeptide also has the above-mentioned function, that is, it also binds to the γ-chain of IL-2 receptor and therefore has an activity of blocking the IL-2 response. The polypeptide of the present invention that has been prepared in the form having Met at its N-terminal may be treated with an enzyme such as aminopeptidase or the like to remove Met from its N-terminal, and the resulting polypeptide also has the above-mentioned function.

If desired, a toxin may be added to the monoclonal antibody or polypeptide of the present invention.

The immunosuppressant of the present invention may contain the above-mentioned monoclonal antibody or polypeptide in an amount of from 0.1% by weight to 100% by weight, preferably from 0.5% by weight to 70% by weight. Therefore, the monoclonal antibody or polypeptide of the present invention may be administered directly as it is or, alternatively, in the form of a medicinal preparation prepared by blending it with an ordinary pharmaceutical carrier. As the pharmaceutical carrier, usable are substances which are ordinarily used in the pharmaceutical field and which do not react with the monoclonal antibody and the polypeptide of the present invention. An injection may be prepared by dissolving the monoclonal antibody or polypeptide of the present invention in water. If desired, it may be dissolved in a physiological saline solution or glucose solution. The injection may optionally contain a buffer, a preservative, a stabilizer and a vehicle. The medicinal preparations of the present invention may contain other therapeutically valuable components.

To administer the immunosuppressant of the present invention, any of peroral, injectable and per-rectal routes may be employed, but preferably it is administered by injection. The dose of the immunosuppressant varies, depending on the administration route, the condition and the age of the patient. In general, the medicine may be administered once to three times a day each in an amount of from 0.001 to 1000 mg, preferably from 0.01 to 10 mg.

The present invention will be explained in more detail by means of the following examples, which, however, are not intended to restrict the scope of the present invention.

EXAMPLE 1

Preparation of recombinant human IL-2 receptor γ-chain polypeptide comprising only extracellular region:

To prepare an IL-2 receptor γ-chain cDNA having a stop codon at its 3'-terminal in the extracellular region, an oligomer 5'-GGACATATGCTGAACACGACAATTCTG-3' (Sequence No. 5) having an NdeI site in its inside and an oligomer 5'-GAAAAGCTTCTATTATGAAGTAT-TGCTCC-3' (Sequence No. 6) having an HindIII site in its inside were integrated, using a DNA synthesizer 380A Model. Both oligomers, being used as the primers, were subjected to PCR (having 20 cycles each comprising denaturation at 94° C., annealing at 55° C. and synthesis at 72° C.) with Taq polymerase, using a plasmid containing a cDNA of IL-2 receptor γ-chain molecule as the template, and using a thermal cycler. (E. coli that had been transformed with this plasmid has been deposited in the National Institute of Bioscience and Human-Technology Agency of Industrial Science and Technology on Feb. 22, 1993 as the deposition code number of FERM BP-4200).

The amplified band with about 0.7 kb was recovered, cut with NdeI and HindIII (made by TAKARA SHUZO CO., LTD.) and ligated with the large fragment of plasmid pFv(TU27)-DE (E. coli that had been transformed with this plasmid has been deposited in the National Institute of Bioscience and Human-Technology Agency of Industrial Science and Technology on Aug. 24, 1992 as the deposition code number of FERM BP-3973) that has been obtained by cutting the plasmid with NdeI and HindIII followed by collecting the large fragment, to construct pIL-2RGS. (See FIG. 1).

Cells of E. coil HB101 that had been transformed with pIL-2RGS were incubated in an M9-Casamino acid medium, whereby the protein was expressed in the cells of E. coli as granules. The cells were ultrasonically disrupted and subjected to centrifugation of 3,000×g to isolate the granules. The granules were dissolved in 6M guanidine hydrochloride and then the protein was refolded by stirring the resulting solution overnight at room temperature in the presence of 3.5M, as the final concentration, of guanidine hydrochloride, 30 μM, as the same, of reduced glutathione and 3 μM, as the same, of oxidized glutathione and under the condition that the protein concentration was 50 μmg/ml. This was subjected to dialysis against 10 mM phosphate buffer containing 150 mM NaCl (pH 7.5) (hereinafter referred to as PBS), to prepare a recombinant human IL-2 receptor γ-chain polypeptide comprising only the soluble extracellular region.

EXAMPLE 2

Preparation of hybridomas:

Female BALB/c mice of from 6 to 8 weeks age were immunized with the recombinant human IL-2 receptor γ-chain polypeptide comprising only the extracellular region, by subcutaneously injecting 100 μg/mouse of the polypeptide along with a Freund's complete adjuvant (made by Bacto Co.). The immunization was repeated additionally two times at intervals of 3 weeks by the same operation, and the blood was collected from the supraorbital vein of each of the immunized mice. The blood was examined according to the method which will be mentioned hereinafter to determine the antibody value by measuring the bound amount of the recombinant human IL-2 receptor γ-chain polypeptide comprising only the extracellular region in the blood. The mice having a high antibody value were finally immunized by the same operation. Three days after the final immunization, the spleen was taken out from each mouse. The cells of the spleen were fused with mouse myeloma cells (SP2/0-Ag14) in the presence of 50% polyethylene glycol #4000 (made by Nacalaitesque Co.), by mixing them at a ratio of 10:1 in terms of the number of the cells.

The fused cells were suspended in RPMI1640 medium (made by Gibco Co.) containing 10% fetal calf serum (made by Gibco Co.) in an amount of 5×10$^6$ cells/ml, and the resulting suspension was put into the wells of a 96-well flat-bottomed plate (made by Corning Co.) containing 5×10$^5$ mouse thymocytes in each well, in an amount of 100 μl/well. After 1, 2, 3 and 6 days, a half of the medium was exchanged for a medium containing hypoxanthine, aminopterin and thymidine (HAT medium), and thereafter the same operation was repeated at intervals of 3 days. About 2 weeks after the cell fusion, the amount of the antibody in the supernatant of the culture in each well where the fused cells (hybridomas) were growing, which had bound to the Lγ cells, as well as the amount of the same which had bound to the Lβ cells was measured, and the hybridomas that bound to only the Lγ cells were cloned by a limiting dilution-culture method.

In addition, in the same manner as mentioned above, the amounts of the hybridoma clones that had bound to the cells in the supernatant of the culture were measured, and anti-IL-2 receptor γ-chain antibody-producing hybridomas were obtained. The supernatants of the culture of the thus-obtained anti-IL-2 receptor γ-chain antibody-producing hybridomas were examined with respect to their potency of inhibiting the biological activity of IL-2 in accordance with the method mentioned below. Precisely, a suspension of ILT-Mat cells that had been suspended in RPMI1640 medium containing 10% fetal calf serum (FCS) in a concentration of 2×10$^5$ cells/ml was put into the wells of a 96-well flat-bottomed micro-plate in an amount of 100 μl/well, 50 μl/well of the supernatant of the culture of the sample to be tested was added to the wells, and 50 μl/well of a human recombinant IL-2 solution that had been prepared by dissolving 200 U/ml of the human recombinant IL-2 in RPMI1640 medium containing 10% FCS was added thereto. The cells were then incubated at 37° C. for 48 hours in the presence of 5% $CO_2$. In the last four hours, the incubation was continued while 1 μCi of $^3$H-thymidine (made by DuPont Co.) was added to the wells, whereupon the intake of the radiation-active amount that had been taken into the cells was measured with a scintillation counter (made by Packard Co.). From the measured amount, the inhibition of the biological activity of IL-2 by the supernatant of the culture was determined. Accordingly, the hybridomas that produce the antibody to IL-2 receptor γ-chain molecules were prepared. The thus-obtained hybridomas are GP-2 (FERM BP-4641), GP-4 (FERM BP-4640), TUGh4 (FERM BP-4642), TUGh5 (FERM BP-4643) and AG14 (FERM BP4648).

The antibody to be produced by hybridoma GP-2 is referred to as antibody GP-2, and that to be produced by hybridoma GP-4 as antibody GP-4. The antibody to be produced by hybridoma TUGh4 is referred to as antibody TUGh4, and that to be produced by hybridoma TUGh5 as antibody TUGh5. The antibody to be produced by hybridoma AG14 is referred to as antibody AG14.

EXAMPLE 3

Preparation of cDNA coding for only V-region of antibody:

5×10$^6$ hybridomas GP-2 or GP-4 were washed with PBS and suspended in an RNA-extracting buffer containing guanidine thiocyanate, N-lauryl sarcosine and EDTA (made by Pharmacia Co.). The hybridoma suspension was layered over cesium chloride solution (ρ=1.51 g/ml, made by Pharmacia Co.) that had been put in a tube, which was subjected to centrifugation at 125,000×g for 16 hours. The volume of the hybridoma suspension was the same as the volume of the cesium chloride solution. After the supernatant was removed by suction, 10 mM tris-hydrochloride solution (pH 7.5) containing 1 mM EDTA was added to the pellet so that the pellet was suspended in the buffer. The resulting suspension was put in a new tube and incubated therein at 65° C. for 5 minutes. ¹⁄₁₀ volume of 2M potassium acetate (pH 5.0) (made by Pharmacia Co.) and three times volume of ethanol (made by Nacalaitesque Co.) were added thereto and allowed to stand at −20° C. overnight. This was subjected to centrifugation at 5,000×g for 20 minutes, the supernatant was removed, and the resulting pellet was washed with 80% ethanol and the dried.

The pellet was dissolved in 10 mM tris-hydrochloride buffer (pH 7.5) containing 1 mM EDTA to obtain a total RNA fraction solution.

Next, to the total RNA fraction solution were added a solution of the 3'-side primer of the V-region of the H-chain of the antibody (1 μm as the final concentration), a solution of the 3'-side primer of the V region of the L-chain of the same (1 μm as the final concentration), a deoxy NTP mixture, a buffer for synthesis of cDNA (made by Amersham Co.), an RNAase inhibitor (made by TAKARA SHUZO CO., LTD.) and a reverse transcriptase (made by TAKARA SHUZO CO., LTD.), and reacted at 42° C. for one hour to produce a cDNA.

To the thus-obtained cDNA were added a 5'-side primer and a 3'-side primer that are used for amplifying the cDNA coding for only the antibody H-chain V-region (each 1 μM as the final concentration), a 5'-side primer and a 3'-side primer that are used for amplifying the cDNA coding for only the antibody L-chain V-region (each 1 μM as the final concentration), a deoxy NTP mixture, a buffer for PCR (made by Perkin-Elmer Co.) and Taq polymerase (made by TAKARA SHUZO CO., LTD.), and subjected to PCR using a thermal cycler (made by Perkin-Elmer Co.). One cycle of the reaction comprised 30 seconds of denaturation (at 94° C.), 30 seconds of annealing (at 55° C.) and one minute of primer extension (at 72° C.), and 30 cycles were repeated. At every cycle, the time for the primer extension was prolonged by 15 seconds.

After the reaction, the reaction mixture was subjected to agarose gel electrophoresis, using 40 mM tris-acetic acid buffer (pH 8.0) containing 1 mM EDTA, and the corresponding cDNA fragments were cut out, extracted and purified with a geneclean kit (made by Bio 101 Co.). The sequences of the primers used for the synthesis of cDNA and for the PCR are shown in FIG. 2 (Sequence Nos. 7 to 10).

EXAMPLE 4

Figure 4:
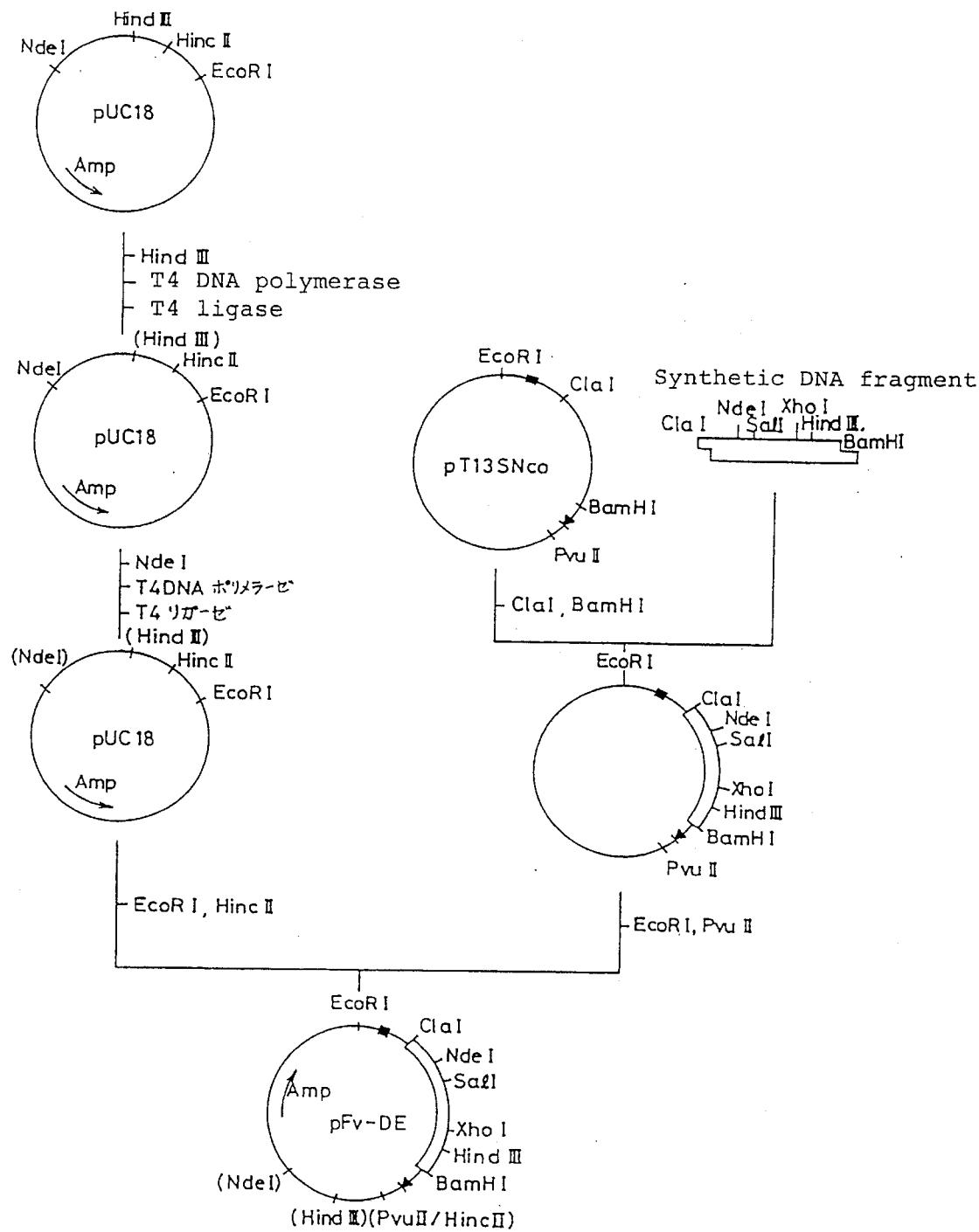
FIG. 4 shows a process of constructing plasmid pFv-DE.

Construction of Expression Vector:

First, as shown in FIG. 4, the large DNA fragment that had been obtained by cutting pT13SNco (*E. coli* AJ-12447 containing this plasmid has been deposited in the National Institute of Bioscience and Human-Technology Agency of Industrial Science and Technology on Apr. 14, 1994 as FERM BP-4635) (described in J. Biochem., Vol 104, page 30, 1988) with restriction enzymes ClaI and BamHI (both made by TAKARA SHUZO CO., LTD.) and the DNA fragment having the sequence shown in FIG. 3 (linker, Sequence Nos. 11 and 12) were ligated together, using a T4 DNA ligase (made by TAKARA SHUZO CO., LTD.). The DNA fragment having the sequence shown in FIG. 3 was produced, using a DNA synthesizer.

Next, the plasmid that had been obtained by ligating the large ClaI-BamHI fragment derived from plasmid pT12SNco and the synthetic DNA fragment was cut with restriction enzymes EcoRI and PvuII (both made by TAKARA SHUZO CO., LTD.) to obtain a small DNA fragment (hereinafter referred to as fragment A, for convenience' sake).

On the other hand, pUC18 (Methods in Enzymology, Vol. 101, page 20, 1983) was cut with a restriction enzyme HindIII, the cut ends were made blunt using a T4 DNA polymerase (made by TAKARA SHUZO CO., LTD.), and this was auto-ligated with a T4 ligase to dismiss the HindIII site therefrom The pUC18 from which the HindIII site had been dismissed was cut with a restriction enzyme NdeI, the cut ends were made blunt using a T4 DNA polymerase (made by TAKARA SHUZO CO., LTD.), and this was auto-ligated with a T4 ligase to dismiss the NdeI site therefrom.

The large DNA fragment that had been obtained by cutting the pUC18, from which both the HindIII site and the NdeI site had been dismissed, with EcoRI and HincII (made by TAKARA SHUZO CO., LTD.) and the fragment A were ligated with a T4 ligase to obtain a plasmid pFv-DE having a pUC replication-starting point.

EXAMPLE 5

Figure 5:
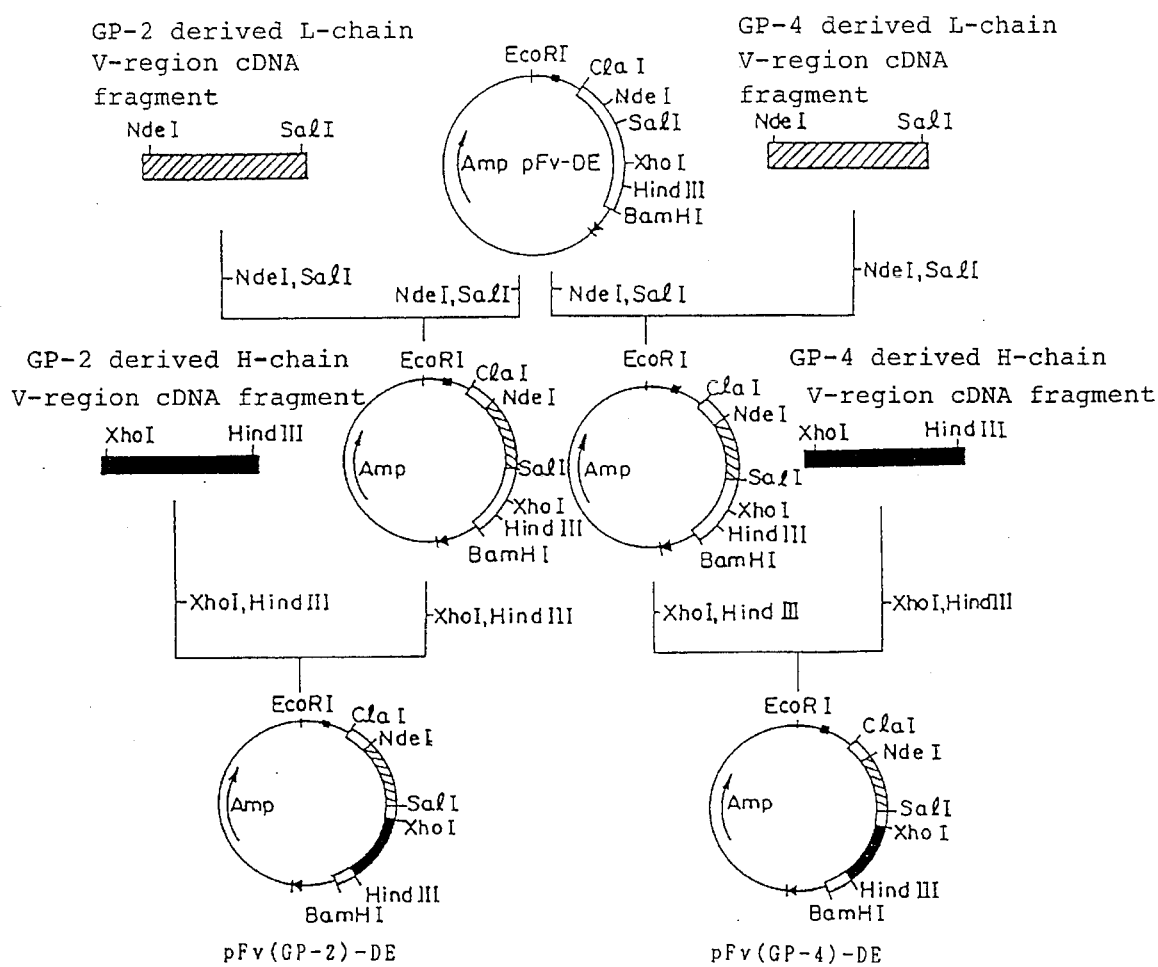
FIG. 5 shows a process of constructing plasmid pFv(GP-2) and plasmid pFv(GP-4).

Insertion of antibody V-region cDNA into pFv-DE, and preparation of microorganisms producing antibody comprising only V-region:

First, as shown in FIG. 5, the pFv-DE was cut with restriction enzymes NdeI and SalI (made by TAKARA SHUZO CO., LTD.) to obtain a large DNA fragment. The large DNA fragment was ligated with the fragment that had been obtained by cutting the L-chain V-region cDNA of GP-2 obtained in Example 3 with NdeI and SalI, using a T4 ligase. Similarly, the large fragment was ligated with the fragment that had been obtained by cutting the L-chain V-region cDNA of GP-4 also obtained in Example 3 with NdeI and SalI, using a T4 ligase.

The thus-obtained two plasmids each were cut with restriction enzymes XhoI and HindIII (made by TAKARA SHUZO CO., LTD.) to obtain large fragments.

Of the large DNA fragments, one containing the L-chain V-region cDNA of GP-2 was ligated with the fraction obtained by cutting the H-chain V-region cDNA of GP-2 that had been obtained in Example 3, with XhoI and HindIII, using a T4 ligase. Similarly, the other large DNA fragment containing the L-chain V-region cDNA of GP-4 was ligated with the fraction obtained by cutting the H-chain V-region cDNA of GP-4 that had been obtained in Example 3, with XhoI and HindIII, using a T4 ligase.

Accordingly, two plasmids expressing an antibody comprising only the V-region, pFv(GP-2)-DE and pFv(GP-4)-DE were obtained.

Subsequently, *E. coli* HB101 was transformed with each of the plasmids to obtain *E. coli* pFv(GP-2)-DE/HB101 (AJ-12844, FERM BP-4636) and *E. coli* pFv(GP-4)-DE/HB101 (AJ-12845, FERM BP-4637), which produce an antibody comprising only the V-region. Three microorganism were deposited with the National Institute of Bioscience and Human-Technology, Agency of Industrial Science and Technology on Apr. 14, 1994.

EXAMPLE 6

Collection of product from microorganisms producing antibody comprising only V-region:

The thus-obtained transformants, *E. coli* pFv(GP-2)-DE/HB101 (AJ-12844, FERM BP-4636) and *E. coli* pFv(GP-4)-DE/HB101 (AJ-12845, FERM BP-4637) each were grown in 5 ml of 2×YT [1.6% trypton, 1% yeast extract (both made by Bacto Co.), 0.5% NaOH, pH 7.0] containing 50 μg/ml of ampicillin, at 37° C. overnight. Next, 5 ml of each of the culture suspensions was seeded in 100 ml of M9-Casamino medium (0.6% $Na_2HPO_4.12H_2O$, 0.3% $KH_2PO_4$, 0.05% NaCl, 0.1% $NH_4Cl$, 0.05% $MgSO_4.7H_2O$), 0.00147% $CaCl_2$, 0.2% glucose, 0.2% Casamino acid, 0.02% L-leucine, 0.02% L-proline, 0.0002% thiamine hydrochloride, 100 μg/ml ampicillin, pH 6.9) and incubated therein at 37° C. for 3 hours. Afterwards, 3-indole-acrylic acid (IAA) was added thereto to have a final concentration of 25 μg/ml therein, and the mixture was further incubated at 37° C. for 20 hours by induction cultivation. A part of the suspension of the grown cells was observed with a phase contrast microscope with magnification of about 1500 powers, which revealed the formation of granules in the cells of *E. coli*.

The suspension of the cells that had been incubated in the manner as mentioned above were subjected to centrifugation to collect the cells, which were then suspended in 50 ml of 30 mM Tris-HCl buffer (pH 7.5) containing 30 mM NaCl. 12.5 ml of an aqueous solution of 0.5M EDTA (pH 8.0) containing 1 mg/ml of lysozyme were added to the suspension, which was then stirred and kept in ice for one hour. Next, the cells were ultrasonically disrupted and subjected to centrifugation at 6000 rpm for 5 minutes to recover the granules therefrom. The granules were dissolved in 6M guanidine hydrochloride solution, and the resulting solution was adjusted so that the concentration of the intended polypeptide became 100 μg/ml and that of guanidine hydrochloride 3.5M. Afterwards, oxidized glutathione and reduced glutathione were added thereto in such a way that the final concentration of the former was 3 μM and that of the latter 30 μM. Subsequently, the pH of the solution was adjusted at 8.0, and the solution was allowed to stand at room temperature for 10 to 16 hours. Finally, the solution was subjected to dialysis against PBS to obtain the intended antibody comprising only the V-region. Both the two transformants were processed in accordance with the above-mentioned process to obtain two antibodies, one being referred to as polypeptide Fv(GP-2) and the other as polypeptide Fv(GP-4).

The molecular weights of the two polypeptides were determined by SDS polyacrylamide gel electrophoresis. The thus-determined molecular weights almost corresponded to those calculated on the basis of the respective amino acid sequences that had been presumed in accordance with Example 7 mentioned below.

Using a protein sequencer, the amino acid sequence of the N-terminal side of each of these polypeptides was sequenced, with the result that the two polypeptides each were identified to have the same amino acid sequence as that presumed in the following Example 7.

EXAMPLE 7

Determination of nucleotide sequence, and presumption of amino acid sequence:

The thus-constructed plasmids pFv(GP-2)-DE and pFv(GP-4)-DE each expressing a polypeptide comprising only the V-region were purified by an alkali SDS method. Using a sequence kit, 7-DEAZA Model (made by TAKARA SHUZO CO., LTD.) and using a commercial sequencing primer M4 or RV (made by TAKARA SHUZO CO., LTD.), the nucleotide sequences of these plasmids were determined. On the basis of the thus-obtained nucleotide sequences, their amino acid sequences were presumed.

Sequence No. 1 in the Sequence Listing indicates the nucleotide sequence of the DNA coding for the polypeptide Fv(GP-2) along with the amino acid sequence thereof to be presumed from the nucleotide sequence. Sequence No. 3 in the same indicates the nucleotide sequence of the DNA coding for the polypeptide Fv(GP-4) along with the amino acid sequence thereof to be presumed from the nucleotide sequence.

As is noted from Sequence No. 2 in the Sequences Listing, Fv(GP-2) is a polypeptide comprised of 244 amino acids, having Met at its N-terminal and Ser at its C-terminal. Fv(GP-4) is a polypeptide comprised of 243 amino acids, having Met at its N-terminal and Ser at its C-terminal.

The L-chain V-region of the antibody to be produced by GP-2 corresponds to the sequence composed of from the 2nd to 109th amino acids in the amino acid sequence of Sequence No. 2 in the Sequences Listing, while the H-chain V-region thereof corresponds to the sequence composed of from 124th to 244th amino acids in the same. The L-chain V-region of the antibody to be produced by GP-4 corresponds to the sequence composed of from the 2nd to 108th amino acids in the amino acid sequence of Sequence No. 4 in the Sequences Listing, while the H-chain V-region thereof corresponds to the sequence composed of from 123th to 243th amino acids in the same.

EXAMPLE 8

Determination of activities of antibody GP-2, antibody GP-4, polypeptide Fv(GP-2) and polypeptide Fv(GP-4):

ILT-Mat cells were suspended in RPMI1640 medium containing 10% FCS in a concentration of $2\times10^5$ cells/ml. The suspension was put into the wells of a 96-well, flat-bottomed micro-plate. The amount of the ILT-Mat cell suspension that had been put into each well was 100 μl/well. The sample solution to be tested was added to the wells. The amount of the sample solution that had been added to each well was 50 μl, and the amount of the antibody or polypeptide contained in the solution was 40 μg/ml.

After having incubated at 37° C. for 30 minutes, 50 μl/well of a solution of human recombinant IL-2 that had been prepared by adding a varying amount of human recombinant IL-2 to RPMI1640 medium containing 10% FCS was added to the wells and the cells were incubated for further 48 hours at 37° C. in the presence of 5% $CO_2$. In the last four hours, the incubation was continued while 1 μCi of $^3$H-thymidine (made by DuPont Co.) was added to the wells.

The intake of the radiation-active amount that had been taken into the cells was measured with a scintillation counter (made by Packard Co.). From the measured amount, determined was the response-blocking potency of each of the antibody GP-2, the antibody GP-4, the polypeptide Fv(GP-2) and the polypeptide Fv(GP-4).

Figure 6:
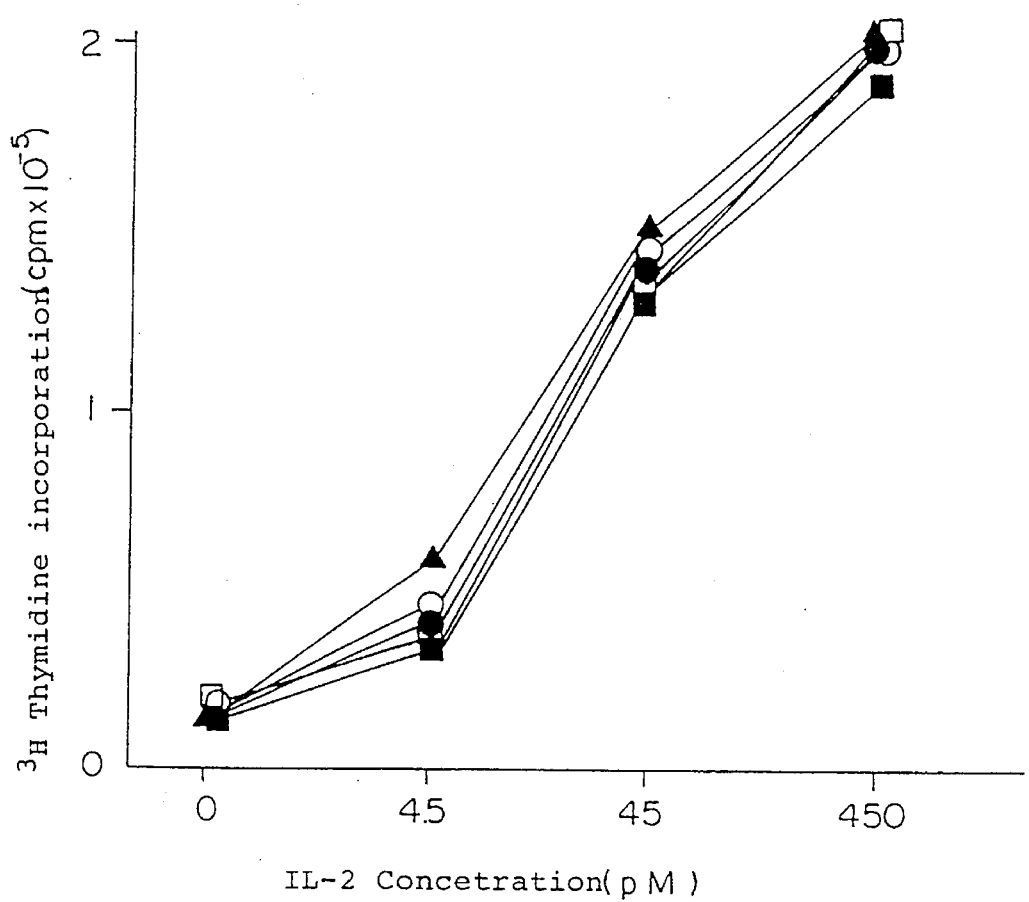
FIG. 6 shows the activities of monoclonal antibodies GP-2 and GP-4 and polypeptides Fv(GP-2) and Fv(GP-4) which inhibit the IL-2 -dependent growth of ILT-Mat cells, wherein Δ indicates the activity of a control antibody, ■ indicates the activity of GP-2, □ indicates the activity of Fv(GP-2), ● indicates the activity of GP-4, and ○ indicates the activity of Fv(GP-4).

The results obtained are shown in FIG. 6, from which it has become clarified that the antibody GP-2, the antibody GP-4, the polypeptide Fv(GP-2) and the polypeptide Fv(GP-4) all have an activity of blocking the IL-2 response in the ILT-Mat cells.

EXAMPLE 9

Determination of IL-2 response-blocking activity of monoclonal antibody GP-2 in the presence of anti-IL-2 receptor α-chain antibody and/or anti-IL-2 receptor β-chain antibody:

ILT-Mat cells were suspended in RPMI1640 medium containing 10% FCS in a concentration of $4\times10^5$ cells/ml. The suspension was put into the wells of a 96-well, flat-bottomed micro-plate. The amount of the ILT-Mat cell suspension that had been put into each well was 100 μl/well. The sample solution to be tested was added to the wells. The amount of the sample solution that had been added to each well was 50 μl, and the amount of each of antibody GP-2, anti-IL-2 receptor α-chain antibody and anti-IL-2 receptor β-chain antibody contained in the sample solution was 40 μg/ml.

After having incubated at 37° C. for 30 minutes, 50 μl/well of a solution of human recombinant IL-2 that had been prepared by adding a varying amount of human recombinant IL-2 to RPMI1640 medium containing 10% FCS was added to the wells and the cells were incubated for further 48 hours at 37° C. in the presence of 5% $CO_2$. In the last four hours, the incubation was continued while 1 μCi of $^3$H-thymidine (made by DuPont Co.) was added to the wells.

The intake of the radiation-active amount that had been taken into the cells was measured with a scintillation counter (made by Packard Co.). From the measured amount, determined was the IL-2 response-blocking potency of the antibody GP-2 in the presence of anti-IL-2 receptor α-chain antibody and/or anti-IL-2 receptor β-chain antibody.

Figure 7:
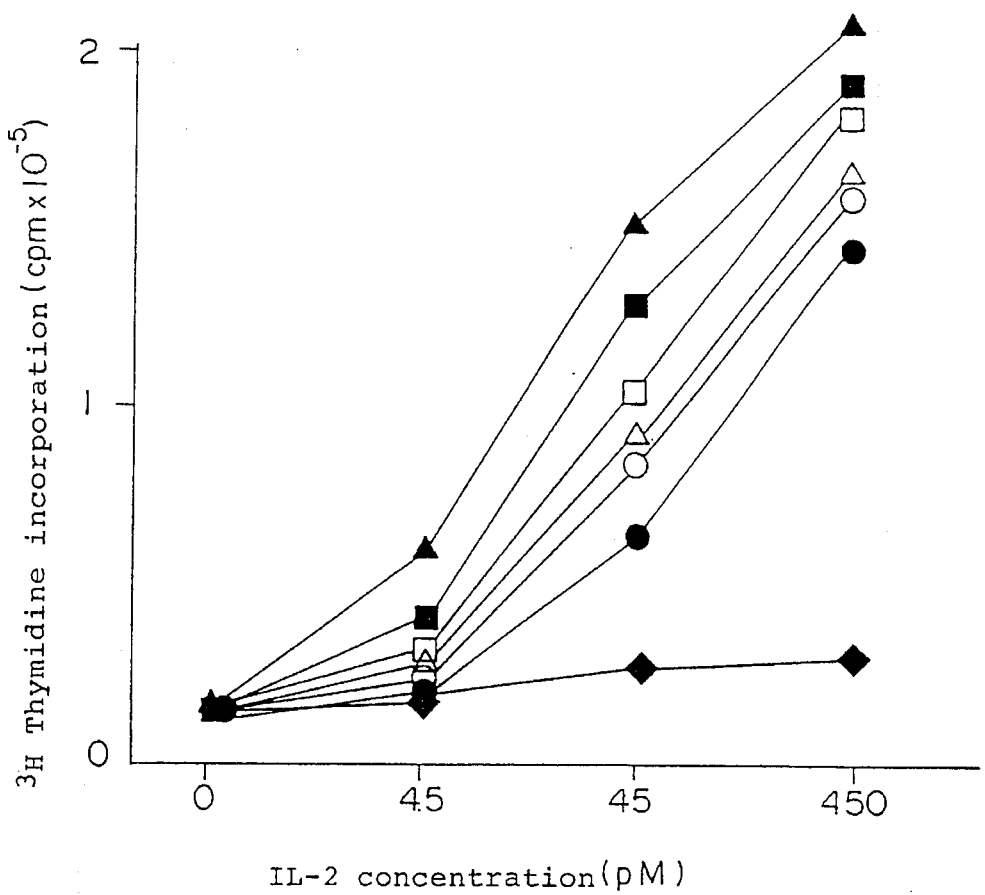
FIG. 7 shows the activity of monoclonal antibody GP-2 which inhibits the IL-2-dependent growth of ILT-Mat cells in the presence of anti-IL-2 receptor α-chain antibody (H31) and/or anti-IL-2 receptor β-chain antibody (TU25), wherein Δ indicates the activity of a control antibody, ■ indicates the activity of GP-2, □ indicates the activity of anti-IL-2R β-chain antibody, ▲ indicates the activity of GP-2 in the presence of anti-IL-2R β-chain antibody, ○ indicates the activity of anti-IL-2R α-chain antibody, ● indicates the activity of GP-2 in the presence of anti-IL-2R α-chain antibody, and ♦ indicates the activity of GP-2 in the presence of both anti-IL-2R α-chain antibody and anti-IL-2R α-chain antibody.

The results obtained are shown in FIG. 7, from which it has become clarified that the antibody GP-2 blocks more effectively the IL-2 response in the ILT-Mat cells in the presence of anti-IL-2 receptor α-chain antibody and/or anti-IL-2 receptor β-chain antibody.

EXAMPLE 10

Determination of activities of antibody TUGh4, antibody TUGh5 and antibody AG14:

ILT-Mat cells were suspended in RPMI1640 medium containing 10% FCS in a concentration of $2\times10^5$ cells/ml. The suspension was put into the wells of a 96-well, flat-bottomed micro-plate. The amount of the ILT-Mat cell suspension that had been put into each well was 100 μl/well. The sample solution to be tested was added to the wells. The amount of the sample solution that had been added to each well was 50 μl, and the amount of the antibody or polypeptide contained in the sample solution was 40 μg/ml.

After having incubated at 37° C. for 30 minutes, 50 μl/well of a solution of human recombinant IL-2 that had been prepared by adding a varying amount of human recombinant IL-2 to RPMI1640 medium containing 10% FCS was added to the wells and the cells were incubated for further 48 hours at 37° C. in the presence of 5% $CO_2$. In the last four hours, the incubation was continued while 1 μCi of $^3$H-thymidine (made by DuPont Co.) was added to the wells.

The intake of the radiation-active amount that had been taken into the cells was measured with a scintillation counter (made by Packard Co.). From the measured amount, determined was the IL-2 response-blocking potency of each of the antibody TUGh4, the antibody TUGh5 and the antibody AG14.

From the results obtained, it has been clarified that the antibody TUGh4, the antibody TUGh5 and the antibody AG14 have an activity of blocking the IL-2 response in the ILT-Mat cells.

REFERENTIAL EXAMPLE

Determination of activity of antibody TUGm2:

Using a monoclonal antibody, TUGm2 (this is anti-mouse IL-2 receptor γ-chain antibody that was prepared by immunizing rats in accordance with the process of Example 2) and/or a monoclonal antibody, anti-mouse IL-2 receptor β-chain antibody (TM-β1; made by Pharmingen Co.), the IL-2 response-blocking potency of these antibodies, if any, in CTLL-2 cells was determined in accordance with the process mentioned below.

Precisely, CTLL-2 cells were suspended in RPMI1640 medium containing 10% FCS in a concentration of $1\times10^4$ cells/ml. The suspension was put into the wells of a 96-well, flat-bottomed micro-plate. The amount of the CTLL-2 cell suspension that had been put into each well was 50 μl/well. The sample solution to be tested was added to the wells. The amount of the sample solution that had been added to each well was 50 μl, and the amount of each antibody contained in the sample solution was 40 μg/ml.

After having incubated at 37° C. for 30 minutes, 50 μl/well of a solution of human recombinant IL-2 that had been prepared by adding a varying amount of human recombinant IL-2 to RPMI1640 medium containing 10% FCS was added to the wells. In addition, RPMI1640 medium containing 10% FCS was further added to the wells, whereupon the final volume of the liquid in each well became 200 μl.

The cells were incubated for further 48 hours at 37° C. in the presence of 5% $CO_2$. In the last four hours, the incubation was continued while 1 μCi of $^3$H-thymidine (made by DuPont Co.) was added to the wells.

The intake of the radiation-active amount that had been taken into the cells was measured with a scintillation counter (made by Packard Co.). From the measured amount, determined was the IL-2 response-blocking potency of the monoclonal antibody TUGm2 and/or the anti-mouse IL-2 receptor β-chain antibody.

Figure 8:
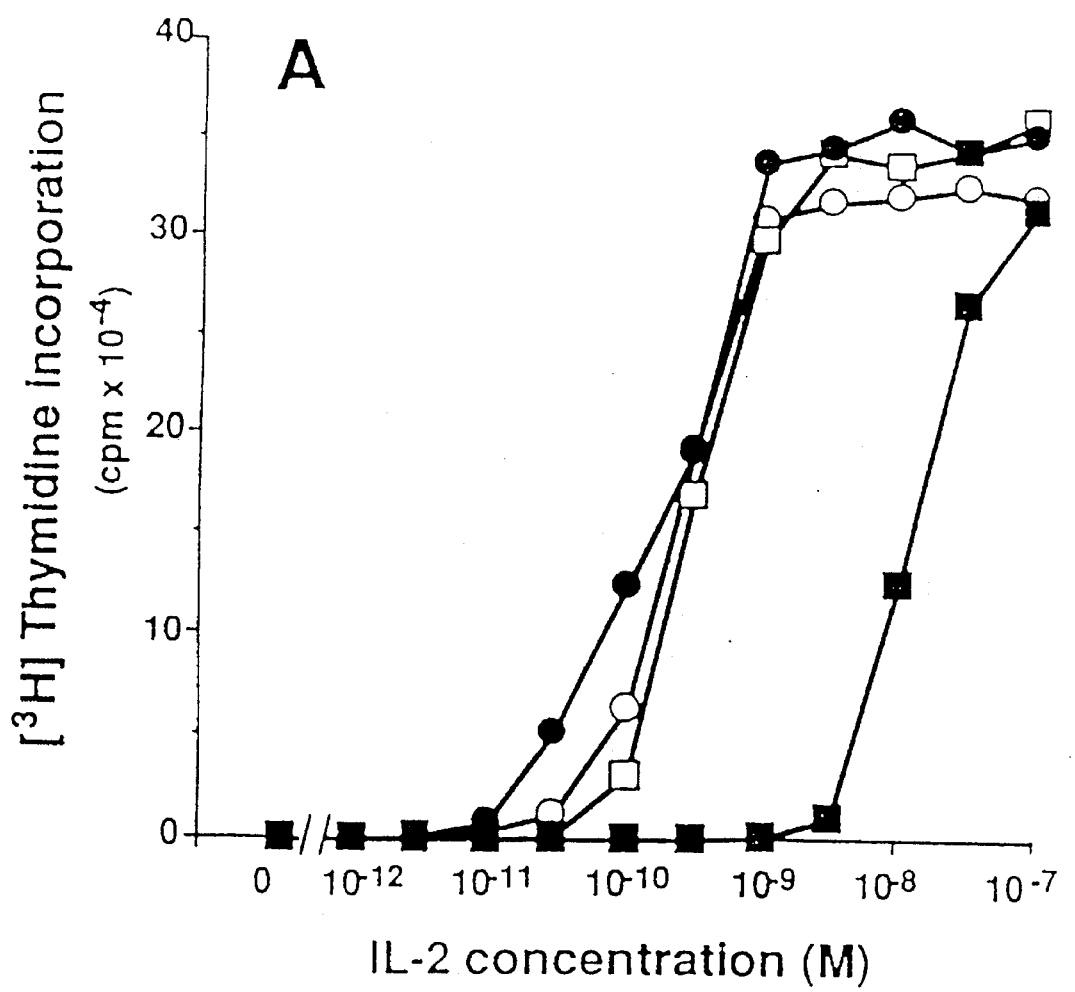
FIG. 8 shows the activity of monoclonal antibody TUGm2 which inhibits the IL-2-dependent growth of CTLL-2 cells by itself or in the presence of anti-mouse IL-2 receptor β-chain antibody, wherein ● indicates the activity of a control sample to which no antibody was added, ○ indicates the activity of TUGm2, □ indicates the activity of anti-IL-2R β-chain antibody, and ■ indicates the activity of TUGm2 in the presence of anti-IL-2R β-chain antibody.

The results obtained are shown in FIG. 8, from which it is clear that the monoclonal antibody TUGm2 blocks the IL-2 response in the CTLL-2 cells in the presence of anti-mouse IL-2 receptor β-chain antibody.

As has been explained in detail hereinabove, the novel polypeptide of the present invention specifically binds to the γ-chain of human interleukin-2 receptor to selectively inhibit the binding of the γ-chain of human interleukin-2 receptor to the β-chain of the same, therefore having an activity of blocking the human interleukin-2 response. The novel polypeptide is a valuable substance which is usable, independently or along with substances capable of inhibiting the binding of interleukin-2 to interleukin-2 receptor, as a medicine effective in preventing the rejection after transplantation and also in curing inflammatory diseases, such as allergic diseases and autoimmune diseases, the likelihood that interleukin-2 participates in transplant rejection and also in such inflammatory diseases having been noted.

While the invention has been described in detail and with reference to specific embodiments thereof, it will be apparent to one skilled in the art that various changes and modifications can be made therein without departing from the spirit and scope thereof.

What is claimed is:

1. A polypeptide which (1) is a monoclonal antibody produced by the hybridoma cells of TUGh4 (FERM BP 4642), TUGh5 (FERM BP4643) or AG14 (FERM BP 4648) and (2) has an activity of inhibiting human interleukin 2 triggered responses which result by binding of the γ chain of human interleukin 2 receptor to the β-chain of human interleukin 2 receptor.

2. An immunosuppressant composition comprising a carrier and a therapeutically effective amount of a polypeptide which (1) is a monoclonal antibody produced by the hybridoma cells of TUGh4 (FERM BP 4642), TUGh5 (FERM BP4643) or AG14 (FERM BP 4648) and (2) has an activity of inhibiting human interleukin 2 triggered responses which result by binding of the γ chain of human interleukin 2 receptor to the β-chain of human interleukin 2 receptor.

\* \* \* \* \*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 732 base pairs
        ( B ) TYPE: nucleic acid
        ( C ) STRANDEDNESS: double
        ( D ) TOPOLOGY: linear ( i i ) MOLECULE TYPE: Other nucleic acid ( i x ) FEATURE:
        ( A ) NAME/KEY: CDS
        ( B ) LOCATION: 1..732

( x i ) SEQUENCE DESCRIPTION: SEQ ID NO:1:

ATG GAC ATC CTG CTG ACC CAG TCT CCA TCA ATC ATG TCT GCA TCT CTA    48

| | | | | | | | | | | | | | | | | |
|---|---|---|---|---|---|---|---|---|---|---|---|---|---|---|---|---|
| Met | Asp | Ile | Leu | Leu | Thr | Gln | Ser | Pro | Ser | Ile | Met | Ser | Ala | Ser | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GGG | GAA | CGG | GTC | ACC | ATG | ACC | TGC | ACT | GCC | AGC | TCA | AGT | GTA | AGT | TCC | 96 |
| Gly | Glu | Arg | Val | Thr | Met | Thr | Cys | Thr | Ala | Ser | Ser | Ser | Val | Ser | Ser | |
| | | | 20 | | | | 25 | | | | | 30 | | | | |

| AGT | TAC | TTG | CAC | TGG | TAC | CAG | CAG | AAG | CCA | GGA | TCC | TCC | CCC | AAA | CTC | 144 |
|---|---|---|---|---|---|---|---|---|---|---|---|---|---|---|---|---|
| Ser | Tyr | Leu | His | Trp | Tyr | Gln | Gln | Lys | Pro | Gly | Ser | Ser | Pro | Lys | Leu | |
| | | 35 | | | | | 40 | | | | | 45 | | | | |

| TGG | ATT | TAT | AGC | ACA | TCC | AAC | CTG | GCT | TCT | GGA | GTC | CCA | GCT | CGC | TTC | 192 |
|---|---|---|---|---|---|---|---|---|---|---|---|---|---|---|---|---|
| Trp | Ile | Tyr | Ser | Thr | Ser | Asn | Leu | Ala | Ser | Gly | Val | Pro | Ala | Arg | Phe | |
| | 50 | | | | 55 | | | | | 60 | | | | | | |

| AGT | GGC | AGT | GGG | TCT | GGG | ACC | TCT | TAC | TCT | CTC | ACA | ATC | AGC | AGC | ATG | 240 |
|---|---|---|---|---|---|---|---|---|---|---|---|---|---|---|---|---|
| Ser | Gly | Ser | Gly | Ser | Gly | Thr | Ser | Tyr | Ser | Leu | Thr | Ile | Ser | Ser | Met | |
| 65 | | | | | 70 | | | | | 75 | | | | | 80 | |

| GAG | GCT | GAA | GAT | GCT | GCC | ACT | TAT | TAC | TGC | CAC | CAG | TAT | CAT | CGT | TCC | 288 |
|---|---|---|---|---|---|---|---|---|---|---|---|---|---|---|---|---|
| Glu | Ala | Glu | Asp | Ala | Ala | Thr | Tyr | Tyr | Cys | His | Gln | Tyr | His | Arg | Ser | |
| | | | | 85 | | | | | 90 | | | | | 95 | | |

| CCG | CTC | ACG | TTC | GGT | GCT | GGG | ACC | AAG | CTG | GAG | CTC | AAA | GTC | GAC | AAA | 336 |
|---|---|---|---|---|---|---|---|---|---|---|---|---|---|---|---|---|
| Pro | Leu | Thr | Phe | Gly | Ala | Gly | Thr | Lys | Leu | Glu | Leu | Lys | Val | Asp | Lys | |
| | | | 100 | | | | | 105 | | | | | 110 | | | |

| TCC | TCA | GGA | TCT | GGC | TCC | GAA | TCC | AAA | AGC | ACG | CAG | GTC | AAA | CTC | GAG | 384 |
|---|---|---|---|---|---|---|---|---|---|---|---|---|---|---|---|---|
| Ser | Ser | Gly | Ser | Gly | Ser | Glu | Ser | Lys | Ser | Thr | Gln | Val | Lys | Leu | Glu | |
| | | 115 | | | | | 120 | | | | | 125 | | | | |

| GAG | TCT | GGA | TCT | GAG | CT.G | GTG | AGG | CCT | GGA | GCT | TCA | GTG | AAG | CTG | TCC | 432 |
|---|---|---|---|---|---|---|---|---|---|---|---|---|---|---|---|---|
| Glu | Ser | Gly | Ser | Glu | Leu | Val | Arg | Pro | Gly | Ala | Ser | Val | Lys | Leu | Ser | |
| | 130 | | | | | 135 | | | | | 140 | | | | | |

| TGC | AAG | GCT | TCT | GGC | TAC | ACA | TTC | ACC | AGC | TAC | TGG | ATG | CAC | TGG | GTG | 480 |
|---|---|---|---|---|---|---|---|---|---|---|---|---|---|---|---|---|
| Cys | Lys | Ala | Ser | Gly | Tyr | Thr | Phe | Thr | Ser | Tyr | Trp | Met | His | Trp | Val | |
| 145 | | | | | 150 | | | | | 155 | | | | | 160 | |

| AAG | CAG | AGG | CAT | GGA | CAA | GGC | CTT | GAG | TGG | ATT | GGA | AAT | ATT | TAT | CCT | 528 |
|---|---|---|---|---|---|---|---|---|---|---|---|---|---|---|---|---|
| Lys | Gln | Arg | His | Gly | Gln | Gly | Leu | Glu | Trp | Ile | Gly | Asn | Ile | Tyr | Pro | |
| | | | | 165 | | | | | 170 | | | | | 175 | | |

| GGT | AGT | GGT | AGT | ACT | AAC | TAC | GAT | GAG | AAG | TTC | AAG | AGC | AAG | GCC | ACA | 576 |
|---|---|---|---|---|---|---|---|---|---|---|---|---|---|---|---|---|
| Gly | Ser | Gly | Ser | Thr | Asn | Tyr | Asp | Glu | Lys | Phe | Lys | Ser | Lys | Ala | Thr | |
| | | | 180 | | | | | 185 | | | | | 190 | | | |

| CTG | ACT | GTA | GAC | ACA | TCC | TCC | AGC | ACA | GCC | TAC | ATG | CAC | CTC | AGC | AGC | 624 |
|---|---|---|---|---|---|---|---|---|---|---|---|---|---|---|---|---|
| Leu | Thr | Val | Asp | Thr | Ser | Ser | Ser | Thr | Ala | Tyr | Met | His | Leu | Ser | Ser | |
| | | 195 | | | | | 200 | | | | | 205 | | | | |

| CTG | ACA | TCT | GAG | GAC | TCT | GCG | GTC | TAT | TAC | TGT | ACA | AGA | AGC | AGC | CGG | 672 |
|---|---|---|---|---|---|---|---|---|---|---|---|---|---|---|---|---|
| Leu | Thr | Ser | Glu | Asp | Ser | Ala | Val | Tyr | Tyr | Cys | Thr | Arg | Ser | Ser | Arg | |
| | 210 | | | | | 215 | | | | | 220 | | | | | |

| AAC | TGG | GTC | TAC | TAT | GCT | ATG | GAC | TAC | TGG | GGT | CAA | GGA | ACC | TCA | GTC | 720 |
|---|---|---|---|---|---|---|---|---|---|---|---|---|---|---|---|---|
| Asn | Trp | Val | Tyr | Tyr | Ala | Met | Asp | Tyr | Trp | Gly | Gln | Gly | Thr | Ser | Val | |
| 225 | | | | | 230 | | | | | 235 | | | | | 240 | |

| ACC | GTC | TCC | TCA | | | | | | | | | | | | | 732 |
|---|---|---|---|---|---|---|---|---|---|---|---|---|---|---|---|---|
| Thr | Val | Ser | Ser | | | | | | | | | | | | | |

( 2 ) INFORMATION FOR SEQ ID NO:2:

( i ) SEQUENCE CHARACTERISTICS:
        ( A ) LENGTH: 244 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asp | Ile | Leu | Leu | Thr | Gln | Ser | Pro | Ser | Ile | Met | Ser | Ala | Ser | Leu |
|---|---|---|---|---|---|---|---|---|---|---|---|---|---|---|---|
| 1 | | | | 5 | | | | | 10 | | | | | 15 | |

| Gly | Glu | Arg | Val | Thr | Met | Thr | Cys | Thr | Ala | Ser | Ser | Ser | Val | Ser | Ser |
|---|---|---|---|---|---|---|---|---|---|---|---|---|---|---|---|
| | | | 20 | | | | 25 | | | | | 30 | | | |

Ser Tyr Leu His Trp Tyr Gln Gln Lys Pro Gly Ser Ser Pro Lys Leu
          35                    40                  45

Trp Ile Tyr Ser Thr Ser Asn Leu Ala Ser Gly Val Pro Ala Arg Phe
    50                   55                  60

Ser Gly Ser Gly Ser Gly Thr Ser Tyr Ser Leu Thr Ile Ser Ser Met
65              70                  75                      80

Glu Ala Glu Asp Ala Ala Thr Tyr Tyr Cys His Gln Tyr His Arg Ser
              85                  90                  95

Pro Leu Thr Phe Gly Ala Gly Thr Lys Leu Glu Leu Lys Val Asp Lys
            100                 105             110

Ser Ser Gly Ser Gly Ser Glu Ser Lys Ser Thr Gln Val Lys Leu Glu
        115             120                 125

Glu Ser Gly Ser Glu Leu Val Arg Pro Gly Ala Ser Val Lys Leu Ser
130                 135                 140

Cys Lys Ala Ser Gly Tyr Thr Phe Thr Ser Tyr Trp Met His Trp Val
145             150                 155                 160

Lys Gln Arg His Gly Gln Gly Leu Glu Trp Ile Gly Asn Ile Tyr Pro
            165                 170                 175

Gly Ser Gly Ser Thr Asn Tyr Asp Glu Lys Phe Lys Ser Lys Ala Thr
            180                 185                 190

Leu Thr Val Asp Thr Ser Ser Thr Ala Tyr Met His Leu Ser Ser
        195                 200                 205

Leu Thr Ser Glu Asp Ser Ala Val Tyr Tyr Cys Thr Arg Ser Ser Arg
    210                 215                 220

Asn Trp Val Tyr Tyr Ala Met Asp Tyr Trp Gly Gln Gly Thr Ser Val
225                 230                 235                 240

Thr Val Ser Ser ( 2 ) INFORMATION FOR SEQ ID NO:3:

( i ) SEQUENCE CHARACTERISTICS:
        ( A ) LENGTH: 729 base pairs
        ( B ) TYPE: nucleic acid
        ( C ) STRANDEDNESS: double
        ( D ) TOPOLOGY: linear ( i i ) MOLECULE TYPE: Other nucleic acid ( i x ) FEATURE:
        ( A ) NAME/KEY: CDS
        ( B ) LOCATION: 1..729

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GAT | ATT | CTG | CTG | ACA | CAG | TCT | CCA | GCC | TCC | CTA | TCT | GCA | TCT | GTG | 48 |
| Met | Asp | Ile | Leu | Leu | Thr | Gln | Ser | Pro | Ala | Ser | Leu | Ser | Ala | Ser | Val | |
| 1 | | | | 5 | | | | | 10 | | | | | 15 | | |
| GGA | GAA | ACT | GTC | ACC | ATC | ACA | TGT | CGA | GCA | AGT | GGG | AAT | ATT | CAC | AAT | 96 |
| Gly | Glu | Thr | Val | Thr | Ile | Thr | Cys | Arg | Ala | Ser | Gly | Asn | Ile | His | Asn | |
| | | | 20 | | | | | 25 | | | | | 30 | | | |
| TAT | TTA | GCA | TGG | TAT | CAG | CAG | AAA | CAG | GGA | AAA | TCT | CCT | CAG | CTC | CTG | 144 |
| Tyr | Leu | Ala | Trp | Tyr | Gln | Gln | Lys | Gln | Gly | Lys | Ser | Pro | Gln | Leu | Leu | |
| | | 35 | | | | 40 | | | | 45 | | | | | | |
| GTC | TAT | AAT | GCA | AAA | ACC | TTA | GCA | GAT | GGT | GTG | CCA | TCA | AGG | TTC | AGT | 192 |
| Val | Tyr | Asn | Ala | Lys | Thr | Leu | Ala | Asp | Gly | Val | Pro | Ser | Arg | Phe | Ser | |
| | 50 | | | | 55 | | | | | 60 | | | | | | |
| GGC | AGT | GGA | TCA | GGA | ACA | CAA | TAT | TCT | CTC | AAG | ATC | AAC | AGC | CTG | CAG | 240 |
| Gly | Ser | Gly | Ser | Gly | Thr | Gln | Tyr | Ser | Leu | Lys | Ile | Asn | Ser | Leu | Gln | |
| 65 | | | | | 70 | | | | | 75 | | | | | 80 | |
| CCT | GAA | GAT | TTT | GGG | AGT | TAT | TAC | TGT | CAA | CAT | TTT | TGG | AGT | ACT | CCG | 288 |
| Pro | Glu | Asp | Phe | Gly | Ser | Tyr | Tyr | Cys | Gln | His | Phe | Trp | Ser | Thr | Pro | |

|  |  |  |  |  |  |  | 85 |  |  |  |  | 90 |  |  |  |  | 95 |  |  |  |
|---|---|---|---|---|---|---|---|---|---|---|---|---|---|---|---|---|---|---|---|---|
| TGG | ACG | TTC | GGT | GGA | GGG | ACC | AAG | CTG | GAG | CTC | AAA | GTC | GAG | AAA | TCC | | | | | 336 |
| Trp | Thr | Phe | Gly | Gly | Gly | Thr | Lys | Leu | Glu | Leu | Lys | Val | Glu | Lys | Ser | | | | | |
|  |  |  | 100 |  |  |  | 105 |  |  |  |  | 110 |  |  |  | | | | | |

```
                                 85                          90                          95
TGG  ACG  TTC  GGT  GGA  GGG  ACC  AAG  CTG  GAG  CTC  AAA  GTC  GAG  AAA  TCC                336
Trp  Thr  Phe  Gly  Gly  Gly  Thr  Lys  Leu  Glu  Leu  Lys  Val  Glu  Lys  Ser
               100                      105                      110

TCA  GGA  TCT  GGC  TCC  GAA  TCC  AAA  AGC  ACG  CAG  GTC  AAA  CTC  GAG  GAG                384
Ser  Gly  Ser  Gly  Ser  Glu  Ser  Lys  Ser  Thr  Gln  Val  Lys  Leu  Glu  Glu
               115                      120                      125

TCT  GGA  CCT  GAG  CTG  GTG  AAG  CCT  GGG  GCT  TCA  GTG  AAG  ATA  TCC  TGC                432
Ser  Gly  Pro  Glu  Leu  Val  Lys  Pro  Gly  Ala  Ser  Val  Lys  Ile  Ser  Cys
               130                      135                      140

AAG  GCT  TCT  GGT  TAC  TCA  TTC  ACT  GGC  TAC  TAC  ATG  CAC  TGG  GTG  AAG                480
Lys  Ala  Ser  Gly  Tyr  Ser  Phe  Thr  Gly  Tyr  Tyr  Met  His  Trp  Val  Lys
145            150                      155                      160

CAA  AGC  CAT  GTA  AAG  AGC  CTT  GAG  TGG  ATT  GGA  CGT  ATT  AAT  CCT  TAC                528
Gln  Ser  His  Val  Lys  Ser  Leu  Glu  Trp  Ile  Gly  Arg  Ile  Asn  Pro  Tyr
               165                      170                      175

AAT  GGT  GCT  ACT  AGC  TAC  AAC  CAG  AAT  TTC  AAG  GAC  AAG  GCC  AGC  TTG                576
Asn  Gly  Ala  Thr  Ser  Tyr  Asn  Gln  Asn  Phe  Lys  Asp  Lys  Ala  Ser  Leu
               180                      185                      190

ACT  GTA  GAT  AAG  TCC  TCC  AGC  ACA  GCC  TAC  ATG  GAG  CTC  CAC  AGC  CTG                624
Thr  Val  Asp  Lys  Ser  Ser  Ser  Thr  Ala  Tyr  Met  Glu  Leu  His  Ser  Leu
               195                      200                      205

ACA  TCT  GAG  GAC  TCT  GCA  GTC  TAT  TAC  TGT  GCA  AGA  GAG  AAT  TAC  TAC                672
Thr  Ser  Glu  Asp  Ser  Ala  Val  Tyr  Tyr  Cys  Ala  Arg  Glu  Asn  Tyr  Tyr
210            215                      220

GGT  AGT  AGC  TAC  GGG  TTT  GCT  TAC  TGG  GGC  CAA  GGG  ACT  CTG  GTC  ACT                720
Gly  Ser  Ser  Tyr  Gly  Phe  Ala  Tyr  Trp  Gly  Gln  Gly  Thr  Leu  Val  Thr
225                 230                      235                      240

GTC  TCT  GCA                                                                                 729
Val  Ser  Ala
```

( 2 ) INFORMATION FOR SEQ ID NO:4:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Asp  Ile  Leu  Leu  Thr  Gln  Ser  Pro  Ala  Ser  Leu  Ser  Ala  Ser  Val
1                   5                        10                       15

Gly  Glu  Thr  Val  Thr  Ile  Thr  Cys  Arg  Ala  Ser  Gly  Asn  Ile  His  Asn
               20                       25                       30

Tyr  Leu  Ala  Trp  Tyr  Gln  Gln  Lys  Gln  Gly  Lys  Ser  Pro  Gln  Leu  Leu
          35                       40                       45

Val  Tyr  Asn  Ala  Lys  Thr  Leu  Ala  Asp  Gly  Val  Pro  Ser  Arg  Phe  Ser
     50                       55                       60

Gly  Ser  Gly  Ser  Gly  Thr  Gln  Tyr  Ser  Leu  Lys  Ile  Asn  Ser  Leu  Gln
65                       70                       75                       80

Pro  Glu  Asp  Phe  Gly  Ser  Tyr  Tyr  Cys  Gln  His  Phe  Trp  Ser  Thr  Pro
               85                       90                       95

Trp  Thr  Phe  Gly  Gly  Gly  Thr  Lys  Leu  Glu  Leu  Lys  Val  Glu  Lys  Ser
               100                      105                      110

Ser  Gly  Ser  Gly  Ser  Glu  Ser  Lys  Ser  Thr  Gln  Val  Lys  Leu  Glu  Glu
               115                      120                      125

Ser  Gly  Pro  Glu  Leu  Val  Lys  Pro  Gly  Ala  Ser  Val  Lys  Ile  Ser  Cys
               130                      135                      140
```

```
Lys Ala Ser Gly Tyr Ser Phe Thr Gly Tyr Tyr Met His Trp Val Lys
145                 150                 155                 160

Gln Ser His Val Lys Ser Leu Glu Trp Ile Gly Arg Ile Asn Pro Tyr
                165                 170                 175

Asn Gly Ala Thr Ser Tyr Asn Gln Asn Phe Lys Asp Lys Ala Ser Leu
            180                 185                 190

Thr Val Asp Lys Ser Ser Thr Ala Tyr Met Glu Leu His Ser Leu
            195                 200                 205

Thr Ser Glu Asp Ser Ala Val Tyr Tyr Cys Ala Arg Glu Asn Tyr Tyr
    210                 215                 220

Gly Ser Ser Tyr Gly Phe Ala Tyr Trp Gly Gln Gly Thr Leu Val Thr
225                 230                 235                 240

Val Ser Ala
```

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:5:

GGACATATGC TGAACACGAC AATTCTG           27

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:6:

GAAAAGCTTC TATTATGAAG TATTGCTCC         29

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:7:

CAGGTSMARC TCGAGSAGTC WGG              23

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:8:

AAGCTTCATG AGGAGACGGT GACCGTGGTC CC      32

( 2 ) INFORMATION FOR SEQ ID NO:9:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:9:

ACAGTCATAA TGTCCCATAT GGAYATYCWG MTGACMCAGT CTCCA    45

( 2 ) INFORMATION FOR SEQ ID NO:10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:10:

GCATCGTCGA CTTTGAGCTC CAGCTTGGTC CC    32

( 2 ) INFORMATION FOR SEQ ID NO:11:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:11:

CGATTAGTAA GGAGGTTTCA TATGTCGACA AATCCTCAGG ATCTGGCTCC GAATCCAAAA    60

GCACGCAGGT CAAACTCGAG AAGCTTG    87

( 2 ) INFORMATION FOR SEQ ID NO:12:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:12:

GATCCAAGCT TCTCGAGTTT GACCTGCGTG CTTTTGGATT CGGAGCCAGA TCCTGAGGAT    60

TTGTCGACAT ATGAAACCTC CTTACTAAT    89